United States Patent [19]
Siddigi et al.

[11] Patent Number: 5,541,113
[45] Date of Patent: Jul. 30, 1996

[54] METHOD FOR DETECTING AN ANALYTE USING AN ELECTROCHEMICAL LUMINESCENT TRANSITION METAL LABEL

[75] Inventors: Iqbal W. Siddigi, Brea; James C. Sternberg, Fullerton, both of Calif.

[73] Assignee: Beckman Instruments, Inc., Fullerton, Calif.

[21] Appl. No.: 125,437

[22] Filed: Sep. 22, 1993

[51] Int. Cl.$^6$ .................................................. G01N 21/00
[52] U.S. Cl. ...................... 436/56; 436/164; 436/172; 422/52; 422/85.05; 422/82.06; 422/82.08
[58] Field of Search ...................................... 436/518, 512, 436/519, 525, 536, 557, 544, 546, 548, 904, 905, 56, 172, 164; 435/4, 5, 6, 7.1, 50; 422/52, 82.05, 82.08, 82.06; 546/2; 250/361 C

[56] References Cited

U.S. PATENT DOCUMENTS

| | | | |
|---|---|---|---|
| 4,280,815 | 7/1981 | Oberhardt et al. | 23/230 B |
| 4,431,919 | 2/1984 | Kostlin et al. | 250/361 |
| 5,068,088 | 11/1991 | Hall et al. | 422/52 |
| 5,147,806 | 9/1992 | Kamin et al. | 436/149 |

FOREIGN PATENT DOCUMENTS

| | | |
|---|---|---|
| 8602734 | 5/1986 | WIPO . |
| 8706706 | 11/1987 | WIPO . |
| 8904302 | 5/1989 | WIPO . |
| 8910551 | 11/1989 | WIPO . |
| 9005296 | 5/1990 | WIPO . |
| 9005301 | 5/1990 | WIPO . |
| 9005302 | 5/1990 | WIPO . |
| 9011511 | 10/1990 | WIPO . |

OTHER PUBLICATIONS

Littig, J. S., et al., "Quantitation of Acridinium Esters Using Electrogenerated Chemiluminescence and Flow Injection" Anal. Chem. (1992), vol. 64, pp. 1140–1144.

Yamashita, K. et al., "Direct Current Electrogenerated Chemiluminescent Microdetermination of Peroxydisulfate in Aqueous Solution", Anal. Chem. (1991), vol. 63, pp. 872–876.

Xie, Y., et al., "Potentiometric Stripping Anaylsis Using Copper (I) and Determination of Chlorine Species", Anal. Chem. (1991), vol. 63, pp. 208–212.

William, D. E., et al. "Electrogenerated Chemiluminescent Determination of Ru(bpy)3 2+ at Low levels", Anal. Chem. (1984) vol. 56, pp. 2413–2417.

Noffsinger, J. B. et al., "Generation of Chemiluminescence upon Reaction of Aliphatic Amines with Tris(2,2'-bipyridine)ruthenium(III)" Anal. Chem. (1987) vol. 59, pp. 565–568.

White, H. S., et al., "Electrogenerated Chemiluminescence. 41, Electrogenerated Chemiluminescence and Chemiluminescence of the Ru(2,2'=bpy)3,2+–S2o8,2–Systems in Acetonitrile–Water Solutions.", Journal of the American Chemical Society (1982), vol. 104 (25), pp. 6891–6895.

(List continued on next page.)

*Primary Examiner*—Jill Warden
*Assistant Examiner*—Sharidan Carrillo
*Attorney, Agent, or Firm*—William H. May; Janis C. Henry

[57] ABSTRACT

A method for detecting an analyte, in an aqueous solution at a physiological pH, by reductive or oxidative/reductive electrochemical luminescence methodologies is disclosed. The method proceeds by labelling the analyte with a transition metal complex, followed by inducing the transition metal label to luminescence by application of a suitable electrical potential to a solution containing the label and the analyte. The transition metal complex can be a tris-ruthenium(bipyridine) complex. A hydroxylamine and/or a halogen-containing moiety can be used to enhance both reductive and/or oxidative electrochemical luminescence of the transition metal complex. The transition metal chelate can be used as a label for the detection of picomolar concentrations of an analyte of interest, such as an analyte present in a sample of a physiological fluid.

36 Claims, 11 Drawing Sheets

OTHER PUBLICATIONS

Kenten, J. H., et al. "Rapid Electrochemiluminescence Assays of Polymerase Chain Reaction Products", Clin. Chem. (1991), vol. 37/9, pp. 1626–1632.

Leland, J. K. et al., "Electrogenerated Chemiluminescence: An Oxidative–Reduction Type ECL Reactions Sequence using Triprophyl Amine", Journal of the Electrochemical Society (1990), vol. 137 #10, pp. 3127–3131.

Rubinstein, I. et al., "Elctrogenerated Chemiluminescent Determination of Oxalate", Anal. Chem. (1983), vol. 55, pp. 1580–1582.

Rubinstein I., et al., :"Electrogenerated Chemiluminescence, 37, Aqueous Ecl Systems Based on Ru(2,2'= bipyridine)3, 2+ and Oxalare or Organic Acids", J. Am. Chem. Soc. (1981 vol. 103, pg.

Blackburn, G. F. et al., "Electrochemiluminescence Detection for Development of Immunoassays and DNA Probe Assays for Clinical Diagnostics", Clin. Chem. (1991) vol. 37/9, pp. 1534–1539.

Kenten, J. H. et al., "Improved Electrochemiluminescent Label for DNA Probe Assays: Rapid Quantitative Assays of HIV–1 Polymerase Chain Reaction Products", Clin. Chem. (1992), vol. 38/6, pp. 873–879.

Bannwarth, W. et al., "219.Bathophenanthroline–ruthenium (II) Complexes as Non–Radioactive Labels for Oligonucleotides which can be measured by Time–Resolved Fluorescnce Techniques" Hel. Chem.Acta. (1988), vol. 71, pp. 2085–2097.

Lytia, F. E., et al., "Chemiluminescence From the Reduction of Aromatic Amine Cations and Ruthenium(III) Chelates", Photochemistry and Photobiology (1971), vol. 13, pp. 123–133.

Brune, S. N. et al., "Role of Electron–Donating/Withdrawing Character, ph, and Stoichiometry on the Chemiluminescent Reaction of Tris(2,2'–bipyridyl) ruthenium (III) with Amino Acids", Anal. Chem. (1992) pp. 166–170.

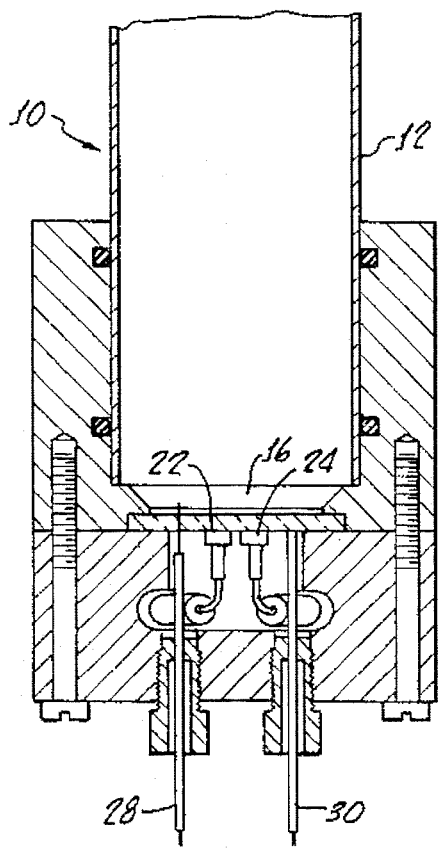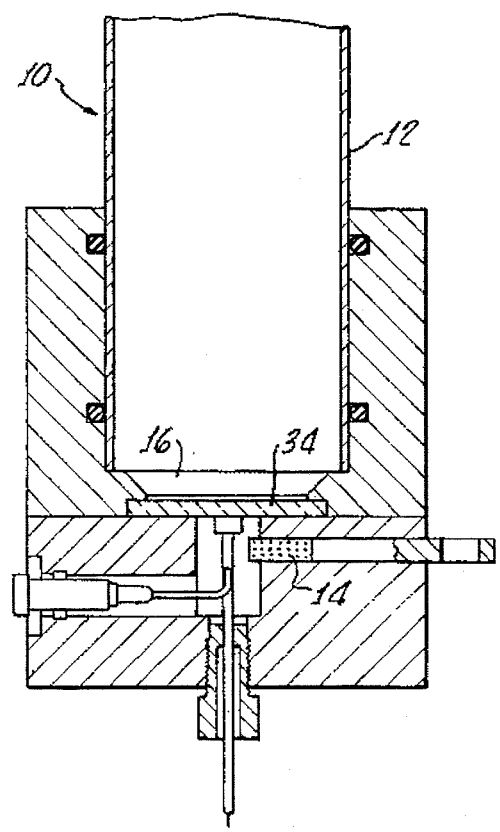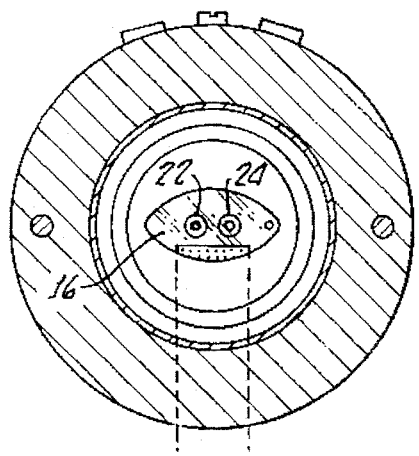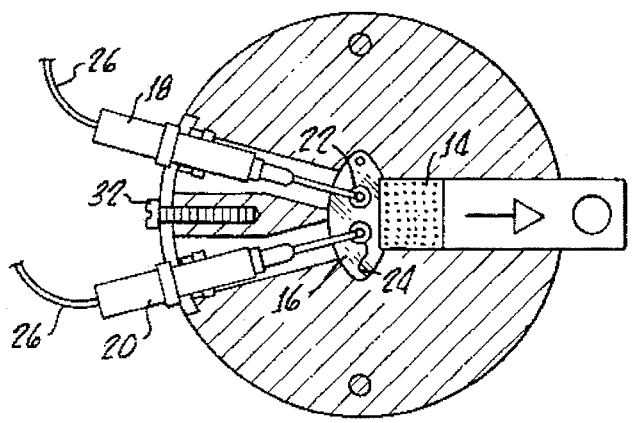

METHOD FOR DETECTING AN ANALYTE USING AN ELECTROCHEMICAL LUMINESCENT TRANSITION METAL LABEL

BACKGROUND

The present invention relates to a method and composition for detecting a luminescent transition metal complex. In particular, the present invention is concerned with the detection of an analyte in an aqueous solution at a physiological pH using an electrochemical luminescent transition metal complex label.

There is a continuing and extensive need to detect and quantify various analytes in a test sample of a physiological fluid. An analyte can be a naturally occurring substance, such as an antibody, antigen, nucleic acid, enzyme, hormone or a metabolite or derivative thereof. An analyte can also be a manmade substance, such as a drug (including both therapeutic drugs and drugs of abuse) or a toxin or a metabolite or derivative thereof. A physiological fluid can be, for example, blood, serum, plasma, urine, amniotic, pleural or cerebrospinal fluid.

An analyte can be detected by labelling the analyte, an analyte analog or a binding partner for the analyte with a detectable label. Preferably, a label is easy to use, can be attached to a variety of substances, thereby enabling its use to detect a variety of analytes, is inexpensive, and has a distinctive and easily detectable signal, permitting rapid differentiation of the label from other substances, including other labels, and thereby analyte detection.

Radioactive labels have been used extensively to detect various analytes. Unfortunately, radioactive labels are expensive, hazardous to use, require sophisticated equipment, have a limited sensitivity, as well as a generally short shelf life, and have stringent disposal requirements.

Non-radioactive labels include labels detectable by spectrophotometric, spin resonance, and luminescence techniques. The use of luminescent material as a label can be advantageous because of high label sensitivity and specificity. Luminescence is a nonthermal emission of electromagnetic radiation by a material upon some form of excitation. The process of luminescence typically involves absorption of energy, excitation and emission of energy, usually in the form of radiation in the visible portion of the spectrum. The type of luminescence can be defined by the excitation means. Thus, electroluminescence is luminescence whereby the excitation source is an electric field. Chemiluminescence is luminescence wherein the excitation source is a chemical reaction.

Electrochemical luminescence (ECL) can occur when an electric field induces a chemical reaction which chemical reaction results in the desired luminescence. In typical ECL methodologies, a reactive species is generated from a stable precursor (i.e. a suitable label) at the surface of an electrode.

A variety of substances can be stimulated to emit detectable electromagnetic radiation via an electrochemical reaction. Some of these substances also have the characteristics, such as solubility and reactivity which can make them suitable for the labelling and detection of different analytes. Such a substance can be called an "ECL label".

Biological molecules, including many analytes present in a sample of a physiological fluid, are typically soluble only in aqueous solution. Additionally, many nonaqueous solvents, including diverse organic and inorganic solvents, can denature or damage labile analytes present in physiological fluids. It is also known that many organic solvents are carcinogenic, volatile and difficult to handle and to dispose of.

Furthermore, the particular configuration and structure of many analytes present in a sample of a physiological fluid necessitates that the aqueous solution in which an analyte is dissolved have a physiological pH, that is a pH between about 6 and about 8. Frequently, the physiological pH of the aqueous solution is maintained at about pH 7 to prevent denaturation or fragmentation of analytes from a physiological fluid.

Thus, most analytes of physiological interest are preferably detected when they are present in an aqueous solution which does not contain any organic or inorganic cosolvents, and which aqueous solution has a physiological pH.

Unfortunately, many substances which exhibit a detectable electrochemical luminescence, and which therefore have potential utility as analyte labels, cannot be used, or cannot be used efficiently, unless present in an organic solvent or an organic cosolvent (such as ether, benzene or acetonitrile), and/or with one or more additional compounds such as a peroxydisulphate or a peroxysulphate. Thus, these substances are unsuitable as ECL labels for the detection of analytes present in physiological fluids.

Various organometallic compounds, including a number of transition metal-organic ligand complexes, have been examined as potential ECL labels for the detection and quantification of analytes present in physiological fluids. Thus, organometallic complexes of ruthenium, osmium, rhenium and/or rhodium can be particularly attractive due, for example, to thermal, chemical and photochemical stability, high emission intensity (which can increase the detection sensitivity) and long emission lifetimes (which can allow use of less expensive measurement instrumentation) of such complexes. It is known that application of an oxidative potential (oxidative ECL) or of a reductive potential (reductive ECL) to a transition metal complex can be used to generate an electrochemical luminescence by the transition metal complex. Specifically, it is known that luminescence of a ruthenium tris-2,2'bipyridine complex (which can be expressed as $Ru(bpy)_3^{2+}$) can be generated using chemical, photochemical, and electrochemical excitation means. Bard, A. J. and Whiteside, G. M., WO 86/02734, which publication is incorporated herein in its entirety.

Unfortunately, there are significant drawbacks and deficiencies with the methodology used in the prior art to generate ECL of a transition metal complex. These problems exist whether oxidative or reductive ECL processes are used to cause the transition metal complex to luminesce, as set forth below.

Oxidative ECL involves the application of a sufficiently positive electric potential to a solution containing a substance capable of participating in an electrochemical luminescence reaction. Bard and Rubinstein, in *J. Am. Chem. Soc.*, (1981), 103, 512–516 discuss an electrochemical oxidation of a ruthenium bipyridyl complex in the presence of oxalate and other organic acids in water. Bard et al., obtained an oxidative ECL by applying a positive or anodic potential greater than about +0.9 volts to an electrode, either continuously or intermittently.

The oxidative ECL method was used by Bard et.al. to detect about $10^{-6}$M of oxalate (*Anal. Chem.*, (1983), 55, 1580–1582) and about $10^{-9}$M of the ruthenium ECL label (*Anal. Chem.*, (1984), 56, 2413–2417, see also WO 86/02734). For Bard et al., no luminescence was reported when a cathodic or negative potential between about 0.0 volts and about −2.0 volts was applied to the reagent solution. Additionally, the oxidative ECL reaction was carried out at a nonphysiological acidic pH to obtain optimal luminescent intensity.

Oxidative ECL in an aqueous buffer solution at a physiological pH has been reported: Leland, J. K. and Powell, M. J., (*J. Electrochem. Soc.*, (1990), 137(10), 3127–3133, and WO 90/05296, May 17, 1990) (which publications are incorporated herein in their entireties) discuss detection of an ECL reaction which utilizes the oxidation of an amine such as tripropylamine and a ruthenium bipyridyl complex as the luminophore. Unfortunately, light emission was observed by Leland et al., even in the absence of the ruthenium complex. Such a background or blank light emission in the oxidative ECL process limits analyte detection to about 100 pM.

Additionally, Noffsinger, J. B. and Danielson (*Anal. Chem.*, (1987), 59, 865–868), and Brune, S. N. and Bobbit, D. R. (Anal. Chem., 1992, 64, 166–170) discuss an oxidative ECL method using various amines and a ruthenium bipyridyl complex. The excited state ruthenium was generated electrochemically, but the luminescence was obtained by subsequent mixing with an amine.

Oxidative ECL has also been discussed by Kenten, J. H., in "Rapid Electrochemiluminescence Assays of Polymerase Chain Reaction Products", *Clin. Chem. 37/9, 1626–1632* (1991), where a tris (2, 2'-bipyridine) ruthenium (II) complex was used as a DNA probe label (available from IGEN, Inc., as the ORIGEN label), and in Kenten, J. H., et. al., in "Improved Electrochemiluminescence Label for DNA Probe Assays: Rapid Quantitative Assays of HIV-1 Polymerase Chain Reaction Products", *Clin Chem.* 38/6, 873–879 (1992), where, a transition metal ECL label comprising a ruthenium polypyridyl chelate (specifically, a tris ruthenium bipyridyl chelate) was used as a DNA probe by attaching the ruthenium complex to the oligonucleotide.

Thus, transition metal complexes have been used as detectable labels for various analytes in oxidative ECL processes. See also Blackburn, G. F., et. al., in "Electrochemiluminescence Detection for Development of Immunoassays and DNA Probe Assays for Clinical Diagnostics", "*Clin. Chem.* 37/9, 1534–1539 (1991), which publication is incorporated herein in its entirety.

Unfortunately, there are significant problems with the use of an oxidative ECL process to detect an analyte present in a sample of a physiological fluid. Generally, the positive voltage potential required to obtain oxidative ECL can result in the evolution of oxygen gas, with resulting deleterious effects to the electrodes used to apply the oxidative potential. Thus, the relatively high positive or anodic oxidative potential required to obtain oxidative ECL can result in the electrodes becoming pitted and eventually dissolved, due at least in part to the oxygen gas evolution.

Additionally, the oxygen gas typically evolved during an oxidative ECL process can remain at or near the electrode surface as a layer of small bubbles lining and insulating the electrode. Such a layer of trapped gas can significantly increase the electrochemical impedance or resistance between the electrodes and can thereby act to prevent or to significantly attenuate the inducement of an ECL reaction at a given electrical potential applied to the aqueous solution. The presence of trapped oxygen gas bubbles over the electrodes can also cause electric arcing between the working and counter electrodes, thereby making analyte detection difficult or impossible.

ECL which might be generated by electrochemical reduction (reductive ECL), less a nodic (oxidative) Potential and electro catalysis have therefore been examined as a way to overcome the problems of analyte detection present with known oxidative ECL processes. Reductive ECL is carried out by applying a sufficiently negative potential to the reagent solution. Such ECL can result in a higher signal output (i.e., more or a more intense light emission) per unit concentration of a stimulated metal chelate. This can allow a higher sensitivity and hence a lower analyte detection limit.

Significantly, the occurrence of oxygen gas evolution with resulting problems of accelerated electrode deterioration and solution impedance increase, is entirely absent or much less significant with reductive ECL, as compared to oxidative ECL processes.

White, H. S. and Bard, A. J., (J. Am. Chem. Soc., (1982), 104, 6891–6895) describe a reductive ECL in a 50% aqueous solution containing an organic co-solvent (such as acetonitrile), peroxydisulfate (a strong oxidizing agent) and a ruthenium bipyridyl complex as the luminophore.

Ege, D. et al., used the method of White et al., for the determination of about $10^{-13}$M ruthenium (Anal. Chem. 1984, 56, 2413–2417, see also WO 86/02734). The reductive ECL reaction was carried out in a 50% acetonitrile/water mixture containing peroxydisulphate. Additionally, to observe any light emission and be able to detect a concentration below about $10^{-8}$M, deaeration of the sample solution was required to remove residual oxygen.

Yamashita, K. P., et al., in "Direct Current Electrogenerated Chemiluminescence. Micro Determination of Peroxydisulfate in Aqueous Solution", Anal Chem. (1991), 63, 872–876, discusses the reductive ECL of a Ru(bipyrazine)$_3$ chelate in aqueous solutions containing 0.1M sodium sulfate. No ECL was observed in the absence of the peroxydisulfate. Significantly, Yamashita, et al., had to prepare solutions of Ru(bipyrazine)$_3$ and peroxydisulfate in the dark to avoid photochemical reaction between the reagents.

Furthermore, White, H. S. and Bard, A. J., (J. Am. Chem. Soc., (1982), 104, 6891–6895) describe a reductive ECL method based on pulsing a platinum electrode repetitively between −0.5 volts and −2.0 volts, using a Ruthenium chelate as the luminophore, in acetonitrile or a partially aqueous solution containing acetonitrile (1:1 by volume) and peroxydisulfate. ECL was not observed in aqueous solutions or in the absence of peroxydisulfate.

Thus, the current art of reductive ECL also has significant shortcomings. As set forth above, the requirements for, at least, one or more organic cosolvents or strong oxidizing agents such as peroxydisulphate in the reagent solution, and deaeration of the solution to allow analyte detection at even a modestly low concentration, severely limits the application of reductive ECL processes for the detection of analytes present in a sample of a physiological fluid below an analyte concentration of about $10^{-9}$M.

Furthermore, although extensive work on reductive ECL processes has been carried out, there has been no report in the art, to the Applicants knowledge, of reductive ECL of a transition metal complex being accomplished in an aqueous solution at a physiological pH, permitting detection below about $10^{-9}$M concentration without the addition of a strong oxidant such as peroxydisulfate and/or removal of dissolved oxygen from the aqueous solution.

It is known that the electrochemical luminescence can be enhanced by various compounds. For example, the electrochemical luminescence of phenyl acridinium-9-carboxylate (as a fluorosulfonate salt) can be enhanced by the addition of cetylammonium bromide to solutions of the acridinium ester. However, optimum electrochemiluminescence has required an elevated pH of from about pH 9 to about pH 12. Littig, J., S., et al., "Quantification of Acridinium Esters Using Electrogenerated Chemiluminescence and Flow Injection" Anal. Chem. (1992), 64, 1140–1144.

What is needed therefore is a method and composition for conducting reductive ECL of a transition metal label in an aqueous solution at a physiological pH. Preferably, the method and composition can permit detection of an analyte below an analyte concentration of about $10^{-9}$M concentration. More preferably, the method can be accomplished without addition of a strong oxidant such as peroxydisulfate to, and/or removal of dissolved oxygen from, the aqueous solution. It would also be advantageous to be able to enhance both reductive and oxidative ECL by a transition metal label through the addition of one or more substances to the aqueous solution prior to stimulation of the transition metal label.

SUMMARY

A composition and method according to the present invention meets these needs. The present method permits a transition metal complex or an analyte employing a transition metal complex label in an aqueous solution, at a physiological pH, to be detected by luminescence induced by electrochemical reduction without an oxidizing agent, in the presence of dissolved oxygen, and by an halide catalyzed electrochemical oxidation.

Additionally, the present method and composition can include a substance capable of enhancing the reductive and/or oxidative electrochemical luminescence by the transition metal label.

The present invention, as in the art, uses an ECL cofactor, such as a tripropylamine. Importantly, we have discovered that by using an ECL facilitator, such as a halide or a hydroxylamine there can be obtained: (1) reductive ECL without first subjecting the aqueous solution to an oxidative potential; (2) reductive ECL after first subjecting the aqueous solution to an oxidative potential, and; (3) oxidative ECL at a significantly lower oxidative potential than that at which an oxidative ECL could previously be obtained.

BRIEF DESCRIPTION OF THE DRAWINGS

The invention will be further understood from the following drawings wherein:

FIG. 1 shows the left side cross-sectional view of an apparatus for detecting an electrochemiluminescence reaction.

FIG. 2 shows the right side cross-sectional view of an apparatus for detecting an electrochemiluminescence reaction.

FIG. 3 shows the top, cross-sectional view of the apparatus of FIG. 1.

FIG. 4 shows the bottom, cross-sectional view of the apparatus of FIG. 1.

DEFINITIONS

Figure 5:
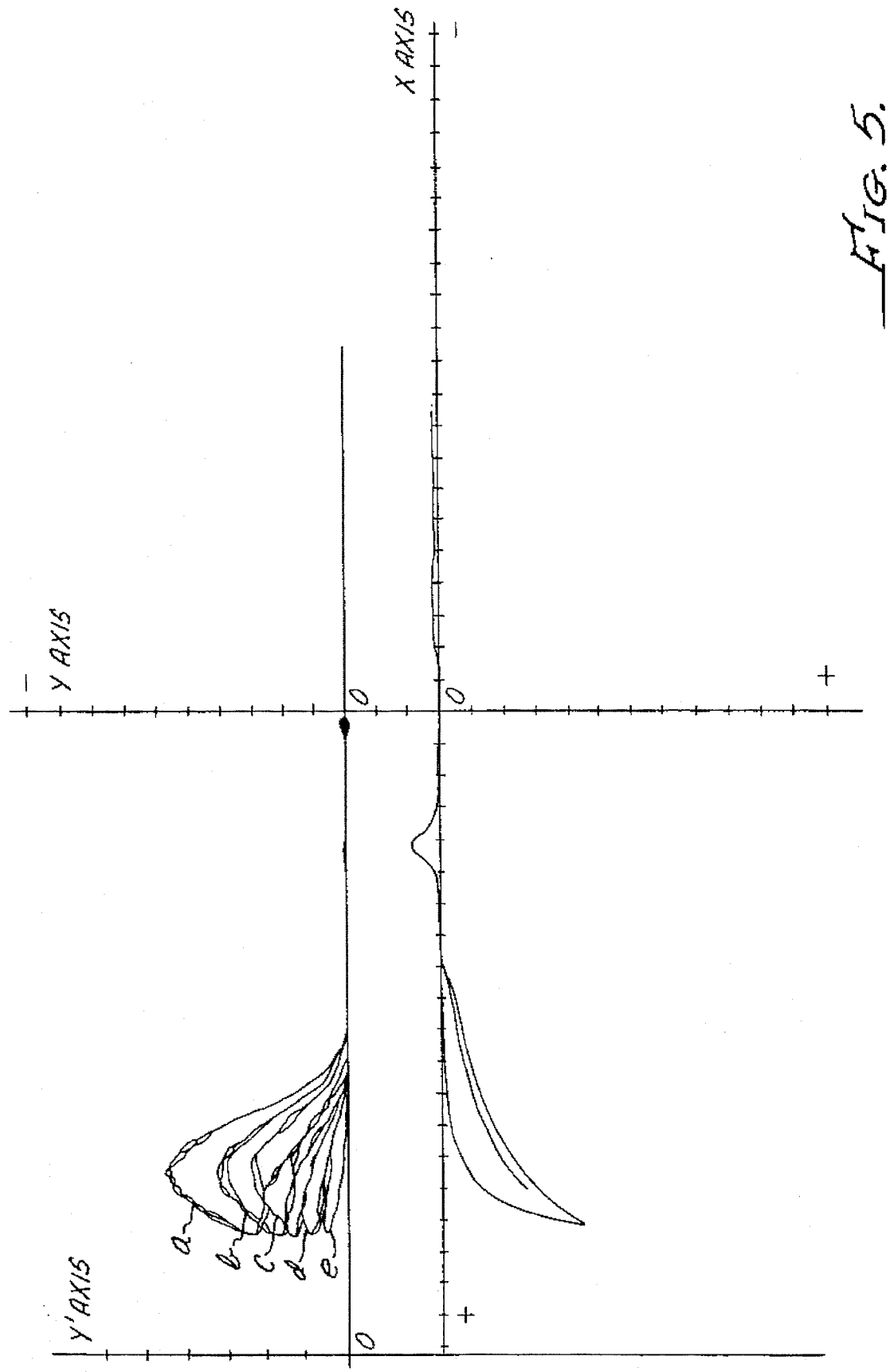
FIG. 5 shows a voltammogram and simultaneous emission profile for a tris-(2,2'-bipyridine) ruthenium II) chloride luminophore.

The term "aqueous solution" means a fluid that uses only water as a solvent to bring any of the substances added to the water into solution. The aqueous solution therefore does not comprise any cosolvent.

The term "ECL cofactor" means a chemical moiety capable of being oxidized and/or reduced in the aqueous solution and of facilitating the reduction and/or oxidation of an ECL label to an excited state.

The term "ECL facilitator" means a chemical moiety capable of altering the oxidative or reductive response of an ECL label, as by lowering the oxidative or reductive potential at which the ECL response can be achieved.

The term "CL label" includes a transition metal complex or chelate through one or more covalent and/or non-covalent bonding interactions with an organic compound, which ECL label is capable of luminescing in the aqueous solution at a physiological pH by electrochemical oxidation or reduction.

The term "negative potential" means a cathodic voltage applied to the aqueous solution containing an electrochemiluminescent (ECL) label. Voltage is measured versus a reference electrode such as a silver/silver chloride electrode.

The term "reductive potential" means a negative voltage sufficient to cause the ECL label to emit detectable electromagnetic radiation.

The term "positive potential" means an anodic voltage versus (the reference electrode) applied to the aqueous solution containing the ECL label.

The term "oxidative potential" means a positive voltage sufficient to cause the ECL label to emit detectable electromagnetic radiation.

The present invention includes a method for detecting an analyte. The method can have the steps of adding a label and an analyte to an aqueous solution, stimulating the label to emit electromagnetic radiation in an electrochemical luminescence reaction by applying a reducing potential to the aqueous solution, and then detecting the analyte by detecting the electromagnetic radiation emitted by the label. The amount of the analyte can also be quantified.

Preferably, the analyte is added to the aqueous solution as a sample of a physiological fluid, because the present method is directly primarily, although not exclusively, to the detection and/or quantification of analytes in various physiological fluids. Prior to adding the analyte to the aqueous solution, the label can be associated with the analyte, as by being directly or indirectly bound to the analyte. The aqueous solution has a physiological pH, between about pH 6 and about pH 8 to assist detection of analytes that are biological molecules. The physiological pH of the aqueous solution can be maintained by addition of a suitable buffer to the aqueous solution. The aqueous solution can be at least about 95% by weight water and at least about 98% by volume water.

The label can comprise a transition metal and an organic ligand. The transition metal can be selected from the group consisting of chromium, ruthenium, rhodium, rhenium, osmium and iridium.

The electromagnetic radiation emitted by the label is preferably light in the visible spectrum, and has an emission maximum at a wavelength between about 200 nm and about 900 nm.

The reducing potential applied to the aqueous solution is at least about −600 millivolts versus a silver/silver chloride reference electrode. An ECL cofactor is typically added to the aqueous solution prior to the stimulating step. The ECL cofactor can be an amine, such as one selected from the group consisting of methylamine, trimethylamine, tripropylamine (i.e. tri-n-propylamine), ethylamine, triethylamine, and propylamine. Additionally, in the method of this invention, an ECL facilitator, which can comprise, for example, a halide, a halogen derivative, or an hydroxylamine, can also be added to the aqueous solution prior to the stimulating step. The hydroxyamine can be selected from the group consisting of hydroxylamine, N-cyclohexyl-hydroxylamine, N-tertbutyl-hydroxylamine, N-methyl-hydroxylamine, and N-isopropyl-hydroxylamine.

The method can also include the step of applying a positive potential to the aqueous solution prior to application of the reducing potential to the aqueous solution. The positive potential applied to the aqueous solution is an oxidative potential, for example a potential of at least about +800 millivolts versus an Ag/AgCl reference electrode.

A more detailed embodiment of the present method for detecting an analyte can have the steps of: preparing an aqueous solution comprising a suitable buffer for maintaining the aqueous solution at a physiological pH; selecting a label comprising a transition metal complex, the label being capable of electrochemiluminescence, i.e. of emitting electromagnetic radiation with an emission maximum between about 200 nm and about 900 nm through an electrochemical reaction; adding an analyte present in a sample of a physiological fluid, the label and an ECL cofactor, such as an amine, and an ECL facilitator, such as a halide or a hydroxylamine, to the aqueous solution, the aqueous solution thereby comprising at least about 95% by weight water and at least about 98% by volume water; stimulating the label to emit electromagnetic radiation in an electrochemiluminescence reaction by application of an electric potential to the aqueous solution; detecting the presence or the absence of the analyte by detecting the electromagnetic radiation emitted, and; quantifying the amount of analyte present in the sample of the physiological fluid.

An important aspect of the present invention, is the discovery of a reductive ECL method and composition for causing electrochemiluminescence of a transition metal complex label in an aqueous solution at a physiological pH, without the addition of a strong oxidant such as peroxydisulfate and/or removal of dissolved oxygen and permitting detection of an analyte of interest at an analyte concentration at or below $10^{-9}$M.

Another important aspect of the present invention, is the discovery of an oxidative ECL method and composition for causing a significantly enhanced electrochemiluminescence of a transition metal label in an aqueous solution and at a lesser positive potential than the oxidation potential of water. For example, the electric potential applied can be an oxidative potential of about 200 millivolts less positive and preferably about 500 millivolts less positive than the potential at which water oxidation generally occurs.

The present invention also includes a method for detecting a transition metal complex. This method can have the steps of adding a transition metal complex to an aqueous solution, stimulating the label to emit electromagnetic radiation in an electrochemical luminescence reaction by applying a reducing potential to the aqueous solution, and detecting the transition metal complex by detecting the electromagnetic radiation it emits.

Also within the scope of the present invention is a composition useful in an electrochemical luminescence assay for an analyte of interest. The composition can comprise: a transition metal complex and an organic compound chelated to the transition metal complex, an ECL cofactor (such as an amine), an ECL facilitator (such as a halide or a hydroxylamine) and a solvent. The solvent can be an aqueous solution which consists essentially of water at a physiological pH. Exposure of the composition to an effective amount of a reducing electric potential can induce the ECL cofactor and the ECL facilitator to chemically react with the complex, thereby inducing the complex to emit electromagnetic radiation.

The present invention also includes within its scope the following methods for generating emission of electromagnetic radiation:

1. A method for generating electrochemical luminescence by a transition metal complex by inducing a transition metal complex in an aqueous solution at a physiological pH to luminesce by applying a reducing electric potential to the aqueous solution.

2. A method for generating electrochemical luminescence by a transition metal complex by inducing a transition metal complex in an aqueous solution at a physiological pH to luminesce by applying an oxidative electrical potential of less than about +1 volt to the aqueous solution.

3. A method for generating electrochemical luminescence by a transition metal complex by inducing a transition metal complex in an aqueous solution at a physiological pH to luminesce by applying an oxidative electrical potential and a reducing electrical potential to the aqueous solution. In this third method, application of the oxidative potential to the aqueous solution can precede application of the reducing electric potential to the aqueous solution.

4. A method for generating electrochemical luminescence by a transition metal complex by inducing the transition metal complex to luminesce by applying an oxidative electrical potential to an aqueous solution at a physiological pH. The aqueous solution can comprise a transition metal complex, and a halide. The halide can act to enhance or to facilitate the desired electrochemical luminescence. Thus, the halide can allow the ECL to be observed at a lower oxidative electrical potential than it would otherwise occur at, and the halide can cause the ECL to be observed at a lesser positive potential than at which water oxidation generally occurs.

5. A method for generating electrochemical luminescence by a transition metal complex by inducing the transition metal complex to luminescence by applying a reductive electrical potential to an aqueous solution at a physiological pH, the aqueous solution comprising the transition metal complex, and a hydroxylamine, the hydroxylamine acting to facilitate the electrochemical luminescence.

6. A method for generating enhanced electrochemical luminescence by a transition metal complex by inducing the transition metal complex to luminescence by applying an electric potential to an aqueous solution at a physiological pH, the aqueous solution comprising the transition metal complex. A selected value of the electric potential applied to the aqueous solution is maintained as a substantially constant electric potential for a time period of between about two seconds and about thirty seconds to enhance the electrochemical luminescence. The electric potential can be an oxidative potential, or a reducing potential. Alternately, the electric potential can be applied as an oxidative potential followed by application of a reducing potential.

DRAWINGS

These and other features, aspects and advantages of the present invention can become better understood from the following description, claims and the accompanying drawings where:

FIG. 1 shows a left side cross-sectional view of an apparatus for carrying out the present method for detecting an analyte and for containing a composition within the scope of the present invention.

FIG. 2 shows a right side cross-sectional view of the apparatus of FIG. 1.

FIG. 3 shows a top view of the apparatus of FIG. 1.

FIG. 4 shows a bottom, cross-sectional view of the apparatus of FIG. 1.

FIG. 5 shows a voltammogram and simultaneous emission profile for a tris-(2,2'-bipyridine) ruthenium (II) chloride luminophore at concentrations of 800 pM, 600 pM, 400 pM, 200 pM and 0 pM (as indicated respectively, by the lower case letters a, b, c, d, and e on FIG. 5. Where the letters a, b, c, d, or e appear on any subsequent Figures, they designate the same concentration of the ruthenium ECL label used in the aqueous solution), in an aqueous solution at pH 7 with 100 mM tripropyl amine, 150 mM phosphate buffer and 0.05% Tween-20, where the voltage was swept from 0.0 v. to +1.6 v. to −0.9 v.

The voltammogram appears in the lower part of the Figure (i.e. without any lower case letter designations). The ECL emission profiles appear in the upper part of the Figure (i.e. with the lower case letter designations)

In FIGS. 5–9, the axes have the following scales: the x axis displays voltage in units of 100 mv per cm (i.e. each of the small vertical lines spaced 1 cm apart along the x axis represents 100 mv of voltage), with positive or anodic voltage being displayed to the left of the y axis, and negative or cathodic voltage being displayed to the right of the y axis.

The central y axis displays units of 10 mv per centimeter. The y' axis along the left edge of the voltammogram graph displays voltage in units of 0.5 mv per cm. The y axis displays light intensity of the ECL emission profile, while the y' axis displays the current from the voltammogram measurement.

Figure 12:
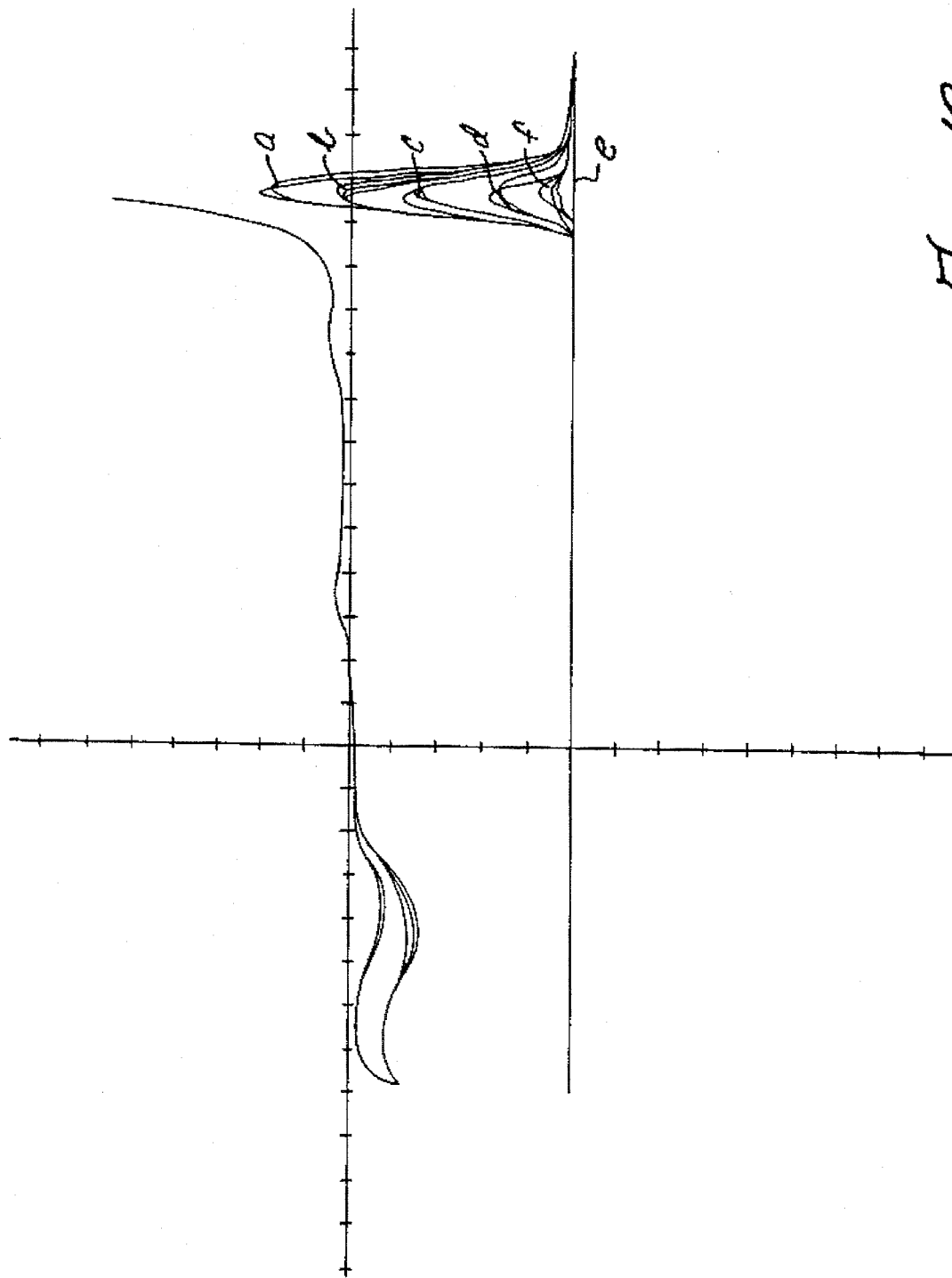
FIG. 12 shows a voltammogram and simultaneous emission profile for a tris-(2,2'-bipyridine) ruthenium (II) chloride luminophore.
Figure 13:
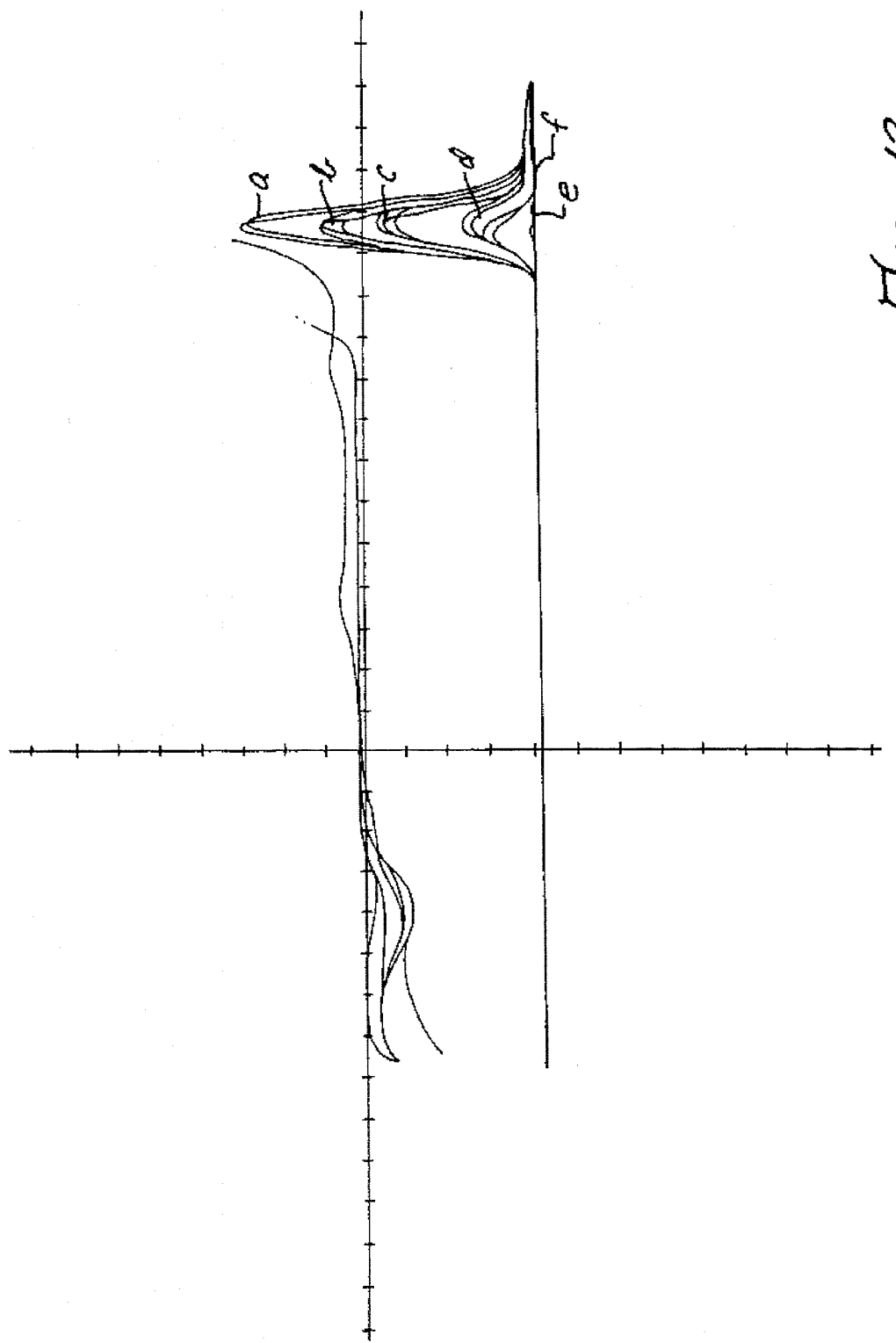
FIG. 13 shows a voltammogram and simultaneous emission profile for a tris-(2,2'-bipyridine) ruthenium (II) chloride luminophore.
Figure 14:
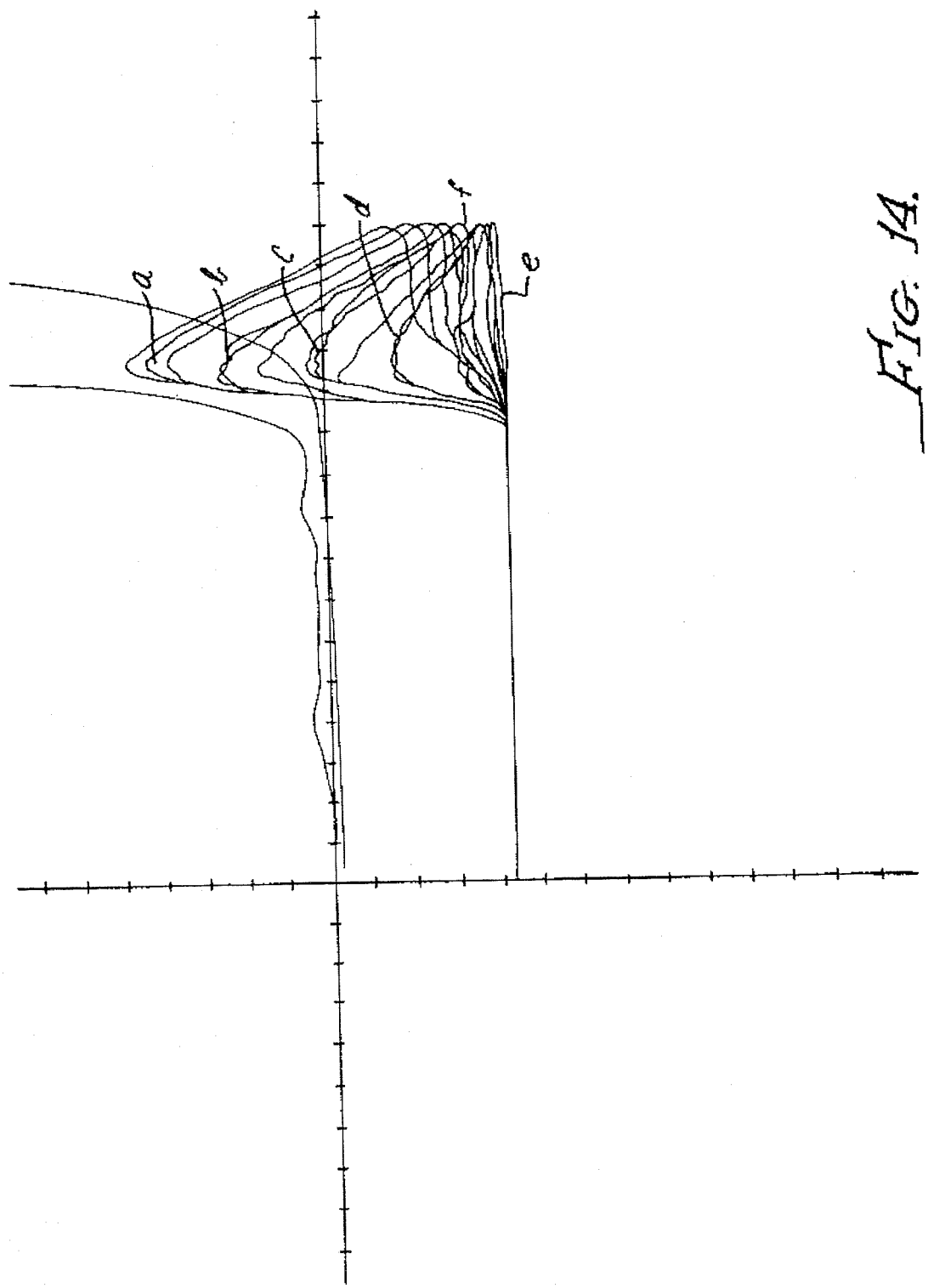
FIG. 14 shows a voltammogram and simultaneous emission profile for a tris-(2,2'-bipyridine) ruthenium (II) chloride luminophore.

In FIG. 5–9 and in FIGS. 12–14, the applied voltage was scanned at the rate of 500 mv per second.

Figure 6:
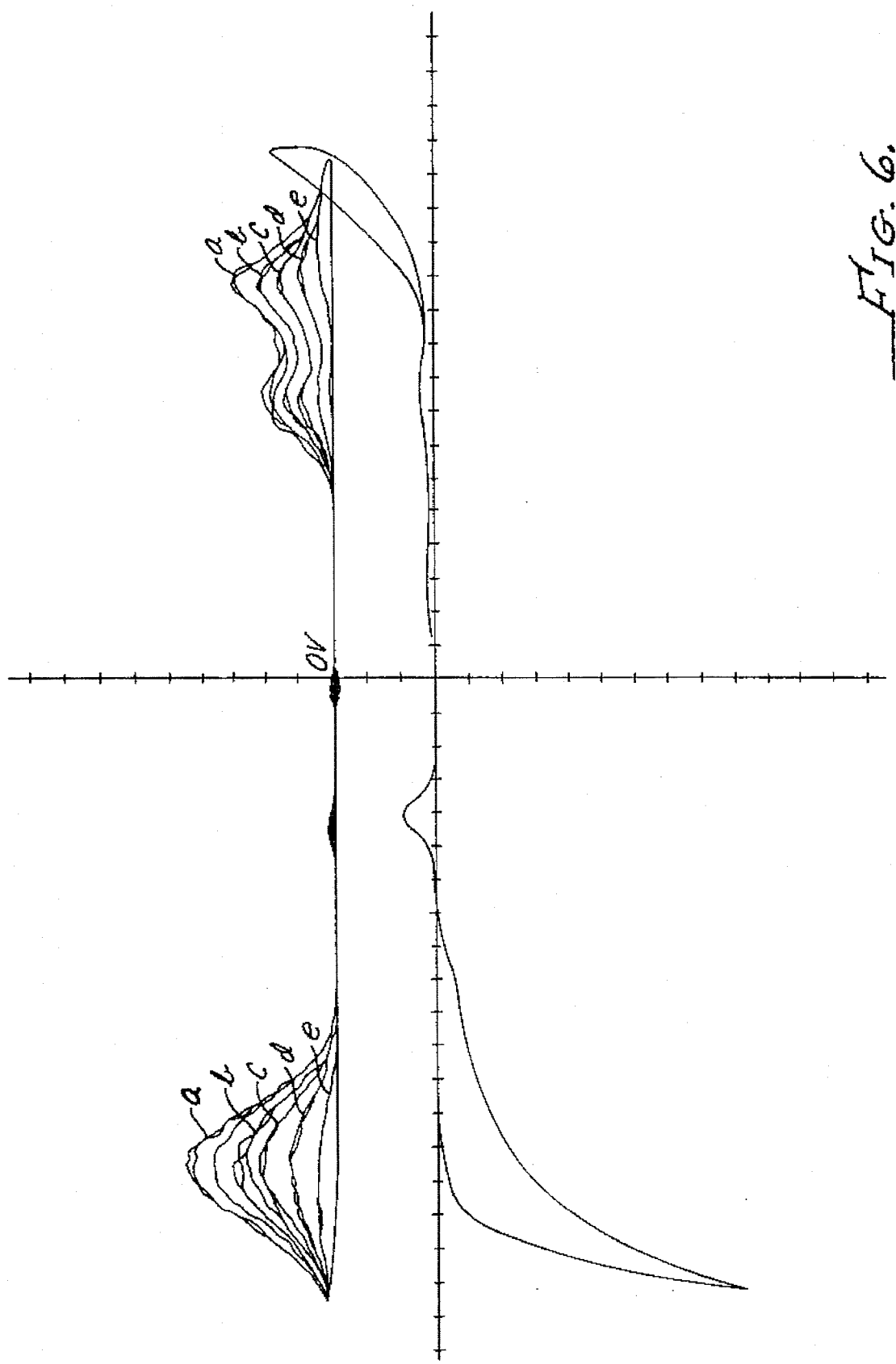
FIG. 6 shows a voltammogram and simultaneous emission profile for a tris-(2,2'-bipyridine) ruthenium (II) chloride luminophore.

FIG. 6 shows a voltammogram and simultaneous emission profile for a tris-(2,2'-bipyridine) ruthenium (II) chloride luminophore at concentrations of 800 pM, 600 pM, 400 pM, 200 pM and 0 pM in an aqueous solution at pH 7 with 100 mM tripropyl amine, 150 mM phosphate buffer and 0.05% Tween-20, where the voltage was swept from 0.0 v. to +1.8 v. to −1.6 v.

Figure 7:
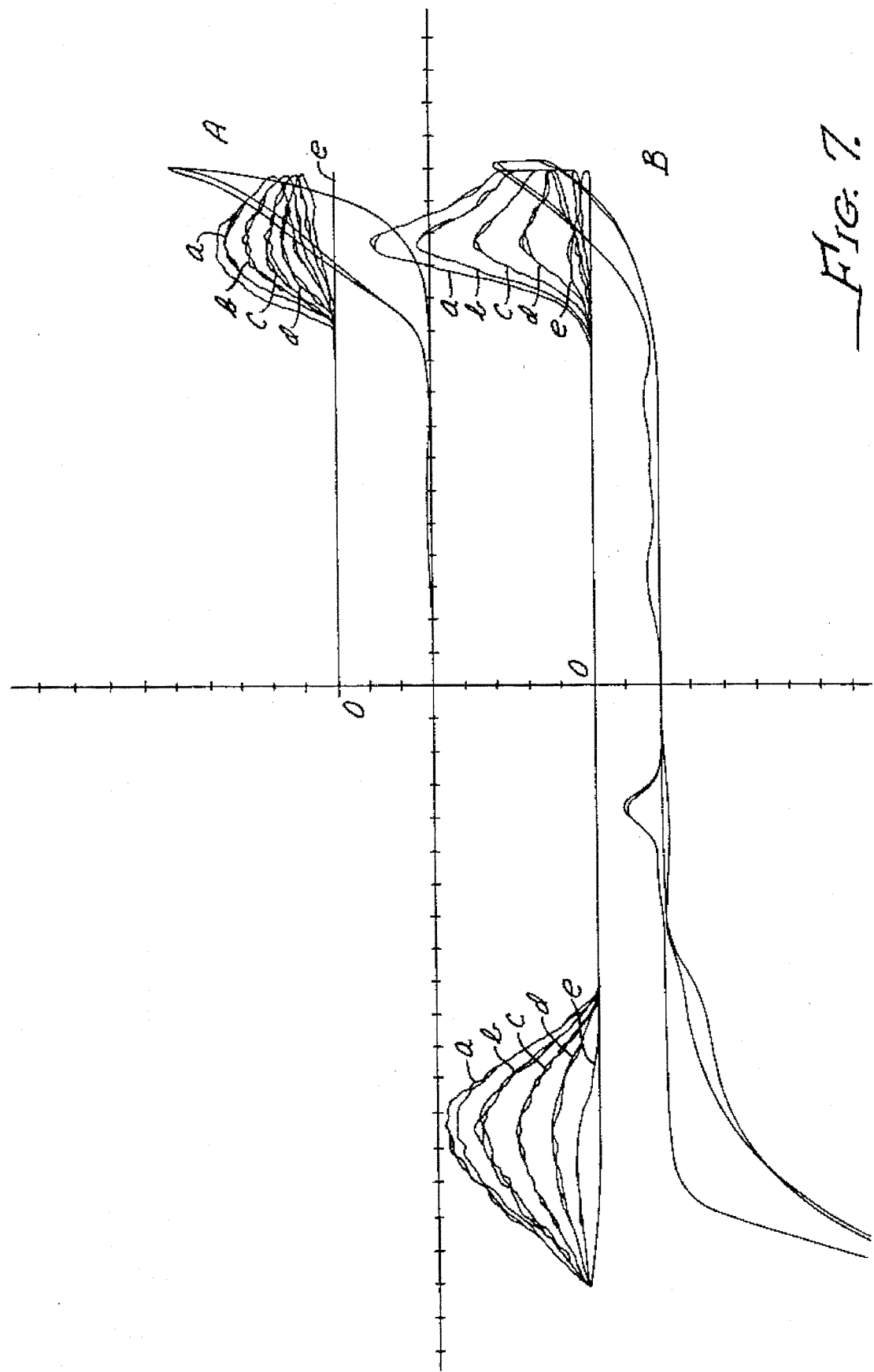
FIG. 7 shows a voltammogram and simultaneous emission profile for a tris-(2,2'-bipyridine) ruthenium (II) chloride luminophore.

FIG. 7 shows a voltammogram and simultaneous emission profile for a tris-(2,2'-bipyridine) ruthenium (II) chloride luminophore at concentrations of 800 pM, 600 pM, 400 pM, 200 pM and 0 pM in an aqueous solution at pH 7 with 100 mM tripropyl amine, 150 mM phosphate buffer, 0.05% Tween-20, and 1 mM hydroxylamine, where the voltage was swept from 0.0 v. to −1.6 v. to 0.0 v. in 7A and the voltage was swept from 0.0 v. to +1.8 v. to −1.6 v. in 7B.

Figure 8:
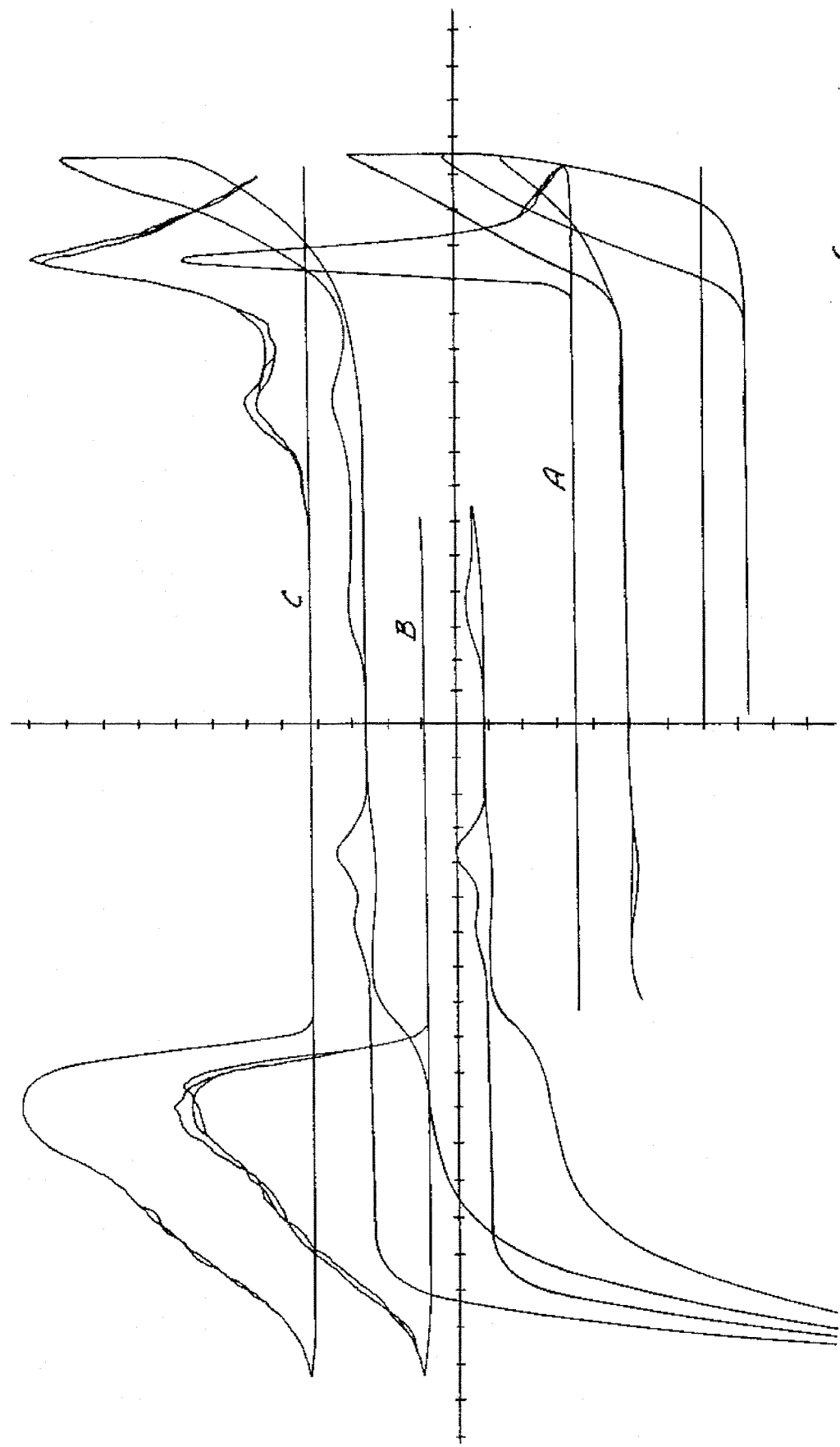
FIG. 8 shows a voltammogram and simultaneous emission profile for a tris-(2,2'-bipyridine) ruthenium (II) chloride luminophore.

FIG. 8 shows a voltammogram and simultaneous emission profile for a tris-(2,2'-bipyridine) ruthenium (II) chloride at a concentration of 800 pM in an aqueous solution at pH 7 with 100 mM tripropyl amine, 150 mM phosphate buffer, 0.05% Tween-20, and 25 mM of sodium chloride, where the voltage was swept from 0.0 v. to +0.8 v. to −1.7 v. in 8A, from 0.0 v. to +1.8 v. to −0.6 v. in 8B, and from 0.0 v. to +1.8 v. to −1.7 v. in 8C.

Figure 9:
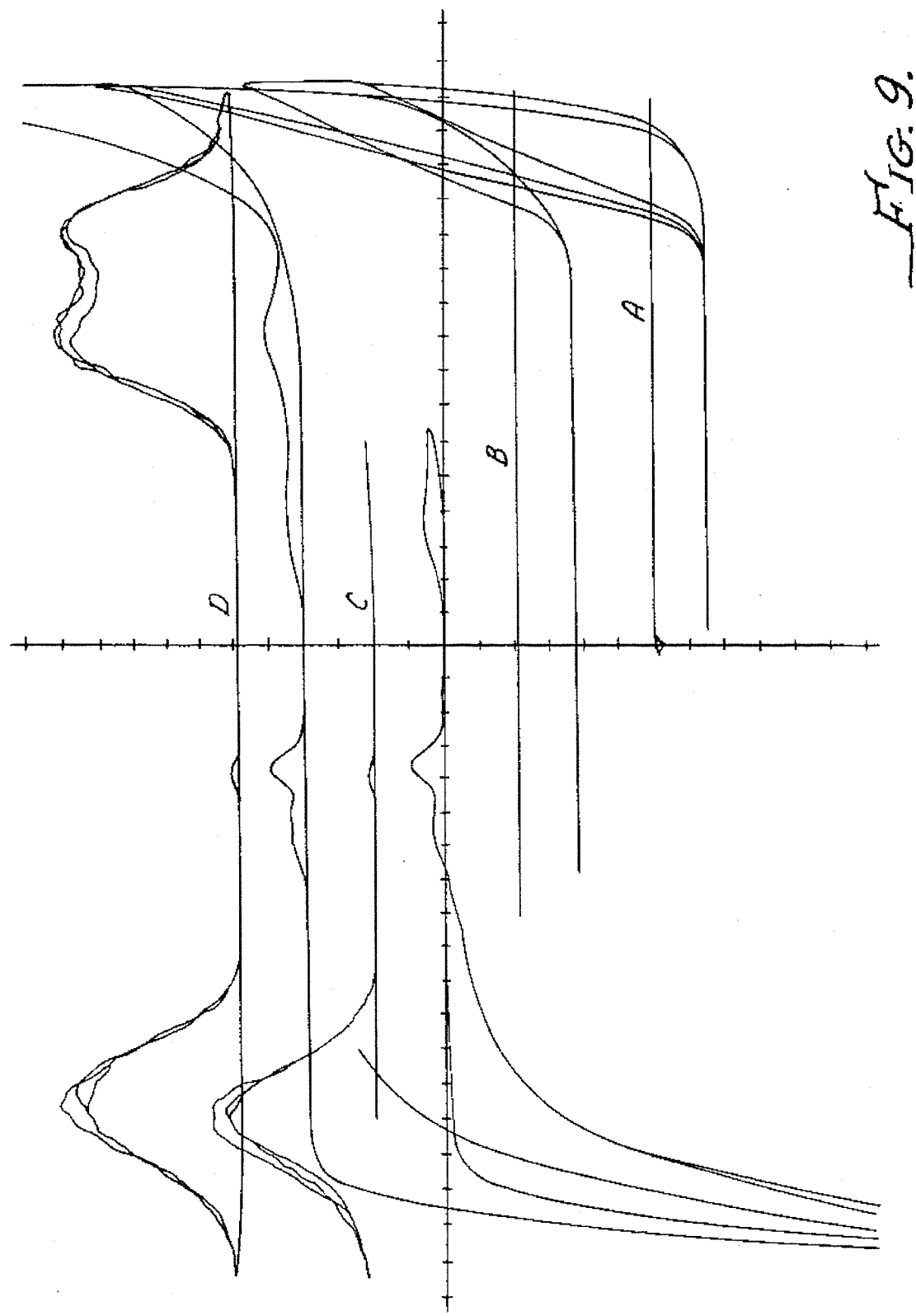
FIG. 9 shows a voltammogram and simultaneous emission profile for a tris-(2,2'-bipyridine) ruthenium (II) chloride luminophore.

FIG. 9 shows a voltammogram and simultaneous emission profile for a tris-(2,2'-bipyridine) ruthenium (II) chloride luminophore at a concentration of 800 pM in an aqueous solution at pH 7 with 100 mM tripropyl amine, 150 mM phosphate buffer and 0.05% Tween-20, where the voltage was swept from 0.0 v. to −1.7 v. to 0.0 v. in 9A, from 0.0 v. to +0.8 v. to −1.7 v. in 9B, from 0.0 v. to +1.8 v. to −0.6 v. in 9C, and from 0.0 v. to +1.8 v. to −1.7 v. in 9D.

Figure 10:
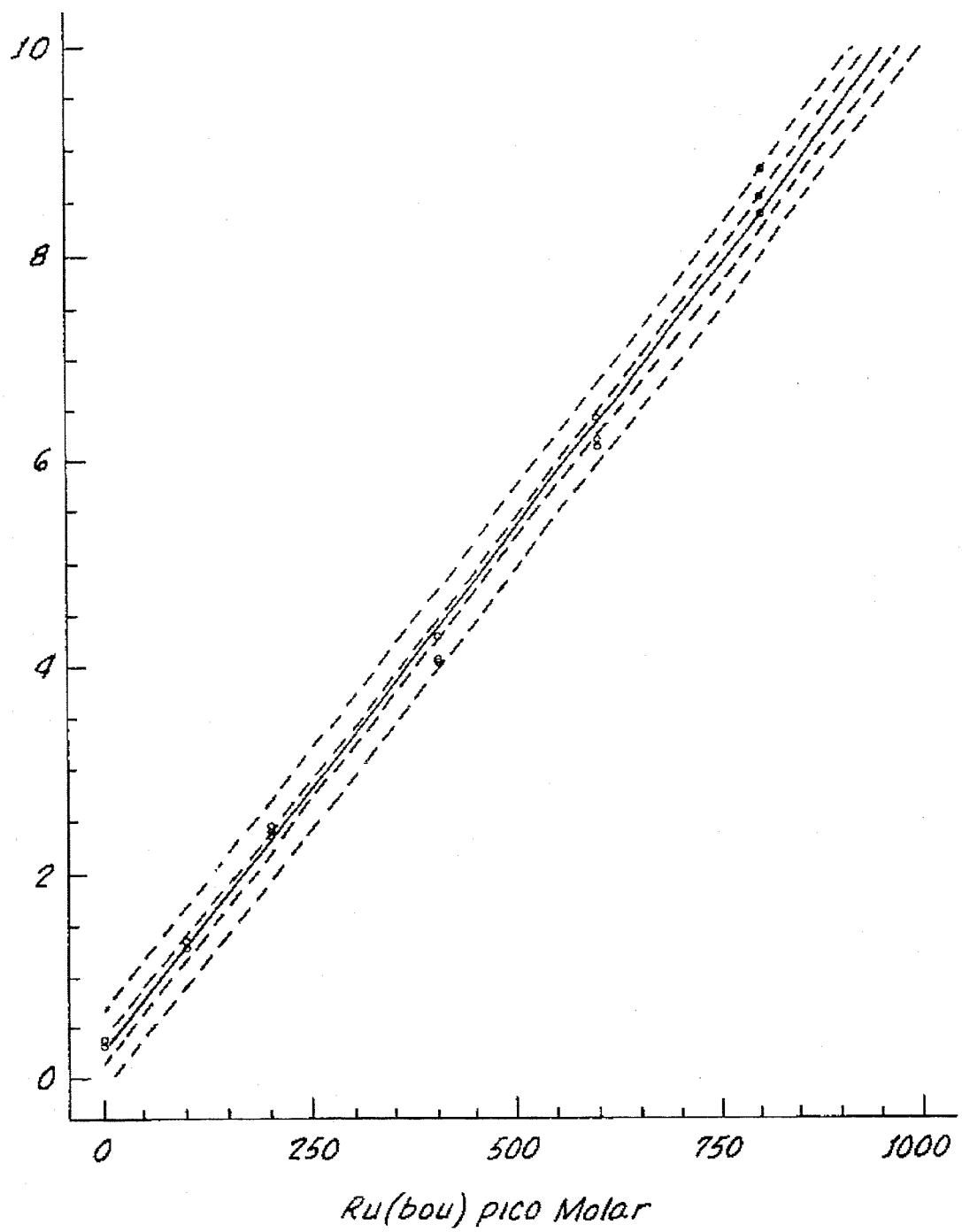
FIG. 10 shows a linear regression plot of a photomultiplier measurement of reductive ECL.

FIG. 10 shows a linear regression plot of photomultiplier measurement of reductive ECL in units of peak height millivolts on the y axis, versus tris-(2,2'-bipyridine) ruthenium (II) chloride ECL label concentration in pico molar amounts on the x axis, where the aqueous solution was at pH 7 and comprised 100 mM tripropyl amine, 150 mM phosphate buffer, 0.05% Tween-20, and 25 mM of sodium chloride.

Figure 11:
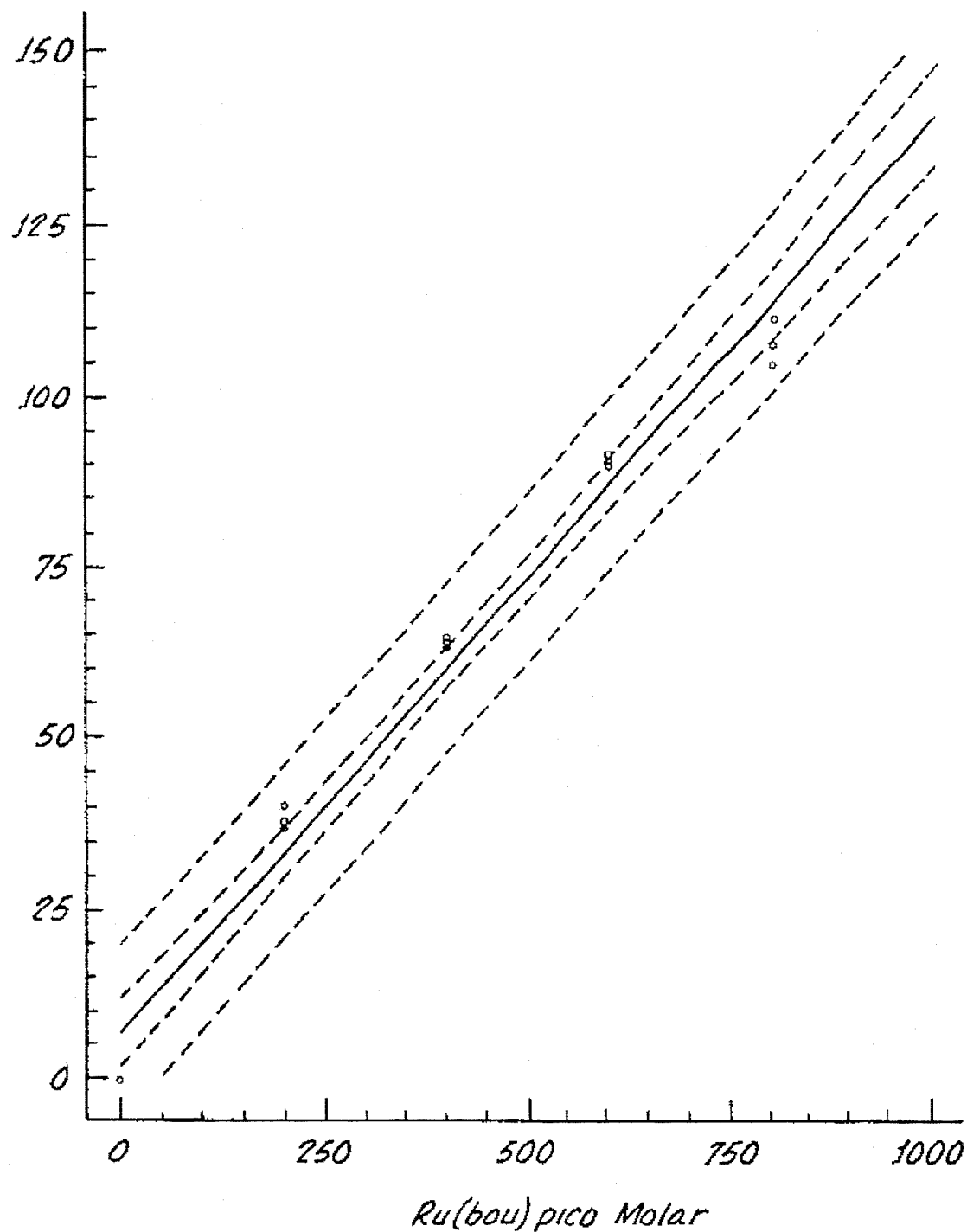
FIG. 11 shows a linear regression plot of a photomultiplier measurement of reductive ECL.

FIG. 11 shows a linear regression plot of photomultiplier measurement of reductive ECL in units of integrated peak area times one thousand on the y axis, versus tris-(2,2'-bipyridine) ruthenium (II) chloride ECL label concentration in pico molar amounts on the x axis, where the aqueous solution was at pH 7 and comprised 100 mM tripropyl amine, 150 mM phosphate buffer, 0.05% Tween-20, and 1 mM of N-cyclohexylhydroxylamine-HCl.

FIG. 12 shows a voltammogram and simultaneous emission profile for a tris-(2,2'-bipyridine) ruthenium (II) chloride luminophore at concentrations of 800 pM, 600 pM, 400 pM, 200 pM, 0 pM and 100 pM (labelled as a, b, c, d, e, and f respectfully) in an aqueous solution at pH 7 with 100 mM tripropyl amine, 150 mM phosphate buffer, 0.05% Tween-20, and 25 mM sodium chloride, where the voltage was swept from 0.0 v. to +0.8 v. to −1.6 v.

The lower case letter f on FIGS. 12–14 indicates a ruthenium ECL label concentration in the aqueous solution of 100 pM. In FIGS. 12–14, the voltammogram graphs, have the following scales: the x axis displays voltage in units of 100 mv per cm, with positive or anodic voltage potential being displayed to the left of the y axis, and negative or cathodic voltage potential being displayed to the right of the y axis. The central y axis displays units of 2 mv per centimeter. The y' axis along the left edge of the voltammogram graph displays voltage in units of 0.5 mv per cm.

FIG. 13 shows a voltammogram and simultaneous emission profile for a tris-(2,2'-bipyridine) ruthenium (II) chloride luminophore at concentrations of 800 pM, 600 pM, 400 pM, 200 pM, 0 pM and 100 pM in an aqueous solution at pH 7 with 100 mM tripropyl amine, 150 mM phosphate buffer, 0.05% Tween-20, and 10 mM ethylamine-HCl, where the voltage was swept from 0.0 v. to +0.8 v. to −1.6 v.

FIG. 14 shows a voltammogram and simultaneous emission profile for a tris-(2,2'-bipyridine) ruthenium (II) chloride luminophore at concentrations of 800 pM, 600 pM, 400 pM, 200 pM, 0 pM and 100 pM in an aqueous solution at pH 7 with 100 mM tripropyl amine, 150 mM phosphate buffer, 0.05% Tween-20, and 1 mM hydroxylamine-HCl, where the voltage was swept from 0.0 v to −1.6 v. to 0.0 v.

DESCRIPTION

The present invention is based upon the discovery that reductive electrochemical luminescence (ECL) of a transition metal complex can be carried out in an aqueous solution at a physiological pH in the presence of dissolved oxygen and without an oxidizing agent. The invention is also based upon the discovery that both oxidative and/or reductive ECL emission by the transition metal complex can be enhanced in various ways, including by adding an amine, such as a hydroxylamine or by adding a halide to the aqueous solution and/or by maintaining a constant electric potential in the aqueous solution for a certain time period.

A low concentration of analyte can be detected by using the present method. For example, a concentration of an analyte of interest as low as about 10 pM in an aqueous solution comprising the analyte can be detected using the present method and composition.

Aqueous Solution

The present invention is directed primarily to the detection and quantification of an analyte, and in particular to the detection and quantification of an analyte present in a sample of a physiological fluid. Many such analytes cannot be effectively, efficiently or practically detected unless the detection methodology proceeds in an aqueous solution at a physiological pH. An important aspect of the present method is the use of an ECL label to detect an analyte from a sample of a physiological fluid in an aqueous solution maintained at a physiological pH.

The aqueous solution in which the ECL reaction is carried out uses water as the only solvent and contains an ECL label, an ECL facilitator, an ECL moderator, a wetting or surface-active agent, and buffering agent to maintain the pH at a desired level.

The water used in the preparation of the aqueous solution has a high purity to prevent undue background ECL. Thus, triple distilled water or the water that has been reverse osmosis purified and that has a resistance measurement of about 18 mega ohms or higher can be suitable.

Buffers for maintaining the pH of an aqueous solution are well known in the art and any one can be used in the present invention provided it does not interfere with the ECL interaction sequence.

Surface active compound are also well known in the art and aid in wetting of metal surfaces with the aqueous reagents for better contact as well as solubilizing reagents. In the present invention, Tween 20 or Triton X-100 at about 0.05% by weight of the aqueous solution are preferred. The type and amount of surface active compound are not critical provided that either does not interfere with the ECL interaction sequence.

The aqueous solution preferably has high electrolytic conduction to facilitate electrochemical reactions. Adequate electrolytic conduction may be achieved by the buffer species present in the aqueous reagent solution or by the addition of a sufficient quantity of a suitable supporting electrolyte to the aqueous solution.

Thus, the aqueous solution comprising water as the only solvent, with buffer, wetting agent and ECL facilitator etc. is typically at least about 95% by weight water, and at least about 98% by volume water.

Transition Metal Complex Label

Detection and quantification of the electrochemical luminescent label enables detection and quantification of an analyte of interest. The label can be associated with the analyte, for the purpose of analyte detection and quantification, in a variety of different ways. For example, the label can be, or become, directly or indirectly attached to the analyte, as in a binding or specific affinity interaction. Alternately, the label can be used to detect a binding partner for the analyte, as in a competitive inhibition immunoassay. Thus, an amount of label detected can be inversely proportional to the amount of analyte present.

The present invention uses an organotransition metal complex as an electrochemical luminescent label for the detection and quantification of an analyte. The label can be stimulated to emit electromagnetic radiation while in an aqueous solution at a physiological pH by the application of an oxidative or reductive voltage potential to the aqueous reagent solution containing an "ECL cofactor" and/or an "ECL facilitator".

Stimulating a label to emit electromagnetic radiation means creating an excited state of the organotransition metal complex label which can then luminesce at a wavelength between about 200 nanometers and about 900 nanometers at an ambient temperature. The particular chemical structure of the organotransition metal complex can change the energy input required to create the luminescent excited state.

Similarly, the wavelength of the emitted electromagnetic radiation can be altered due to the nature of the transition metal component of the complex. Thus, an ECL label in accordance with the present invention is induced to emit electromagnetic radiation by stimulating it into an excited electromagnetic state. This is carried out by exposing the ECL label and an ECL cofactor and/or an ECL facilitator in an aqueous reagent solution to electrochemical oxidation and reduction. The potential at which electrochemical excitation of the label occurs depends upon a number of factors such as the chemical structures of the label, the ECL cofactor, the ECL facilitator, the pH of the aqueous solution and the nature of the electrode material used to transfer electrons.

The transition metal is preferably selected from Group 8 Periodic Table elements and more preferably from the transition metals chromium, ruthenium, rhodium, rhenium, osmium, and iridium because these transition metals are believed to be capable of ECL and to be useful as an ECL label, when chelated with a suitable organic ligand. Such complexes are particularly preferred because they have desirable chemical and physical characteristics such as long emission lifetimes, thermal and chemical stability and susceptibility to electrochemiluminescence.

In a particularly preferred embodiment of the present invention ruthenium or osmium can be used as the transition metal component of the complex because ruthenium and osmium have known utility as ECL labels. A ruthenium transition metal can be used as a chelate of a tris-ruthenium bipyridine. Such labels are commercially available, can be used for analyte detection and have an emission maximum at about 680 nanometers.

The organic portion of the complex or label forms a chelate with one or more transition metal atoms. The organic ligand portion of the label can be any one of a number of compounds, including anthracene and polypyridyl molecules and other heterocyclic organic compounds. Such organic compounds are commercially available and are known to chelate various transition metals.

Preferred ligands are aromatic heterocyclic nitrogen-containing species, such as, for example, bipyridyl, bipyrazyl, terpyridyl, and phenanthrolyl. The ligand can be substituted and suitable substituents can include alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide.

Suitable particular ligands include bis [(4,4'-carbomethyoxy)-2,2 '-bipyridine]-2-[3-(4-methyl-2,2'-bipyridine-4-yl)proply]-1,3-dioxolane ruthenium (II); bis (2,2' bipyridine) [4-(butan-1-al)-4'-methyl-2,2'-bipyridine] ruthenium (II); bis (2,2'-bipyridine) [4-(4'-methyl-2,2'-bipyridine-4'-yl)-butyric acid] ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis (2,2'-bipyridine) [4-(4'-methyl-2,2'-bipyridine)-butylamine] ruthenium (II); bis (2,2'bipyridine) [1-bromo-4-(4'-methyl-2,2'-bipyridine-4-yl)-butane]ruthenium (II); and bis (2,2'-bipyridine) maleimido-hexanoic acid, 4-methyl-2,2'-bipyridine-4'-butylamide ruthenium (II).

A composition in accordance with the present invention can comprise two or more labels. Each of the labels can be induced to emit electromagnetic radiation of a wavelength different from the other label or labels. In another embodiment, the labels can be induced to emit electromagnetic radiation by exposure to energy of a value different from the energy value(s) at which the other label or labels can emit radiation. In this manner it is possible to detect two or more different analytes in the sample.

Enhancement of Electrochemical Luminescence

The present invention uses an ECL cofactor and can also use an ECL facilitator to assist transformation of the ECL label to an excited state. The ECL cofactor is preferably an amine, such as tripropylamine, and the ECL facilitator can be a hydroxylamine and/or a halogen-containing substance. We have characterized and disclose herein a variety of suitable ECL cofactors and ECL facilitators.

We have found that a variety of amines can be used as ECL facilitators in practicing the present invention.

Amines which are advantageously utilized in the present invention are aliphatic amines, such as primary, secondary and tertiary alkyl amines. Tripropyl amine is a preferred amine that can provide a high-intensity emission of electromagnetic radiation, enabling a sensitive and accurate detection of an analyte.

We have also discovered that an ECL facilitator, such as a halide or a halide-containing compound can be used to enhance the electrochemical luminescence by a selected ECL label. Thus, we have found that adding a halide such as a chloride or bromide ion to the aqueous solution permits obtaining oxidative ECL at a potential lower than that at which an oxidative ECL could previously be obtained.

We have further discovered that adding a halide such as a chloride or bromide ion to the aqueous solution makes it possible to obtain reductive ECL, which is only observed following a sweep of the potential in a positive direction, which need not be sufficient to invoke oxidative ECL.

Furthermore, we have discovered that a hydroxylamine can also be used induce reductive ECL, even in the absence of first sweeping the potential to a positive voltage. Thus, adding a hydroxylamine to the aqueous solution was found to make reductive ECL possible in the aqueous solution at a physiological pH without adding an oxidant such as peroxydisulfate and removal of dissolved oxygen.

Types of Analytes

The present invention can be used to detect a transition metal ECL label and thereby to detect an analyte. The label can be attached to an analyte of interest. Additionally, failure to detect the label can indicate absence of a particular analyte. The label can become attached to an analyte in, for example, an antigen-antibody, ligand-receptor interaction, or nucleic acid hybridization reaction.

The analyte can be, for example, a whole cell, an antigen, subcellular particle, virus, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, nonbiological polymer (preferably soluble), synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in a sample.

The ECL label can be attached to, for example, an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions by methods known to the art.

Whole cells may be animal, plant, or bacterial, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multienzyme complexes, and other particles which can be derived from living organisms. Nucleic acids include, for example, chromosomal DNA, plasmid DNA, viral DNA, and recombinant DNA derived from multiple sources. Nucleic acids also include RNA's, for example messenger RNA's, ribosomal RNA's and transfer RNA's. Polypeptides include, for example, enzymes, transport proteins, receptor proteins, and structural proteins such as viral coat proteins. Preferred polypeptides are enzymes and antibodies. Particularly preferred polypeptides are monoclonal antibodies. Hormones include, for example, insulin and T4 thyroid hormone. Pharmacological agents include, for example, cardiac glycosides.

The analyte can include synthetic substances and analyte analogs such as synthetic polypeptides, nucleic acids, and synthetic membranes, vesicles and liposomes.

Instrumentation

A method of the present invention can be further explained by reference to an apparatus suitable for carrying out the present method. The present method can detect an analyte by detecting an electrochemiluminescent label in a variety of ways. Thus, the label can be detected by, for example, measuring: the rate of energy input into an aqueous solution containing the label; the electric current when the luminescent species of the label is generated electrochemically; the rate of reductant or oxidant utilization when the luminescent species of the label is generated, and; absorption of electromagnetic energy can be used to detect and quantify the label. Preferably, the label is detected by measuring the electromagnetic radiation emitted by the label. These measurements can be made as continuous, rate-based measurements, or cumulative over time measurements.

A rate-based measurement can be made using a suitable photomultiplier, photodiode or phototransistor. A cumulative measurement can be made using, for example, a photographic film, a CCD camera or by integrating a signal from a photomultiplier, photodiode or phototransistor.

FIGS. 1 to 4 disclose an advantageous apparatus for generating and detecting electrochemiluminescence of the disclosed ECL label. However, the methods of the present invention are not limited to application with apparatus 10, but rather can be implemented with other types of apparatus including a working electrode or other triggering surface to provide electrochemical energy to trigger electrochemiluminescence. While the methods of the invention can be carried out in a static or flow-through mode, apparatus 10 is a flow-through cell.

Apparatus 10 has a light detection/measurement device 12, which can be a photomultiplier tube, photodiode, charge coupled device, photographic film or emulsion or the like. A magnet 14 can be used for harvesting magnetic particles from the aqueous solution, such as magnetic particles associated with, for example, an antigen-antibody complex. The aqueous solution is held by the electrochemical cell 16. Electrodes 18 and 20 provide the working and counter electrodes. Each of the electrodes 18 and 20 has a gold electrode surface 22 and 24 (although platinum, carbon or other materials may also be suitable) respectively, that contacts the aqueous solution within the cell 16. Electrically conductive wires 26 permit an electric potential to be supplied to the electrodes 18 and 20 and to be applied to the aqueous solution. The aqueous solution enters the cell 16 through fluid inlet 28, and leaves the cell through fluid outlet 30.

A third or reference electrode 32 typically has a silver/silver chloride electrode surface. The reference electrode 32 provides a fixed voltage to measure the voltage applied to the working electrode.

The aqueous solution can be pumped into the cell 16 using a peristaltic pump such as a Gilson "mini pulse 2™" peristaltic pump. A flow rate of about 1 milliliter per minute is generally suitable. The pump is turned off during label detection. The recorder used was an X-Y, Y' recorder manufactured by Kipp Zonen, where the y-axis shows the measurement of applied current, and the y'-axis shows the measurement of luminescence output.

Included in apparatus 10 is a lightproof housing inside of which the various components of the apparatus can be disposed to shield a photomultiplier tube 12 from any external light and a potentiostat to impose a controlled supply voltage signals to the electrodes 18 and 20. The potentiostat also measures the actual imposed voltage as well as the electrochemical current flowing between the electrodes.

Additionally, apparatus 10 includes a window 34 formed from a material that is substantially transparent at the wave length of ECL light generated by the system. Window 34 is therefore advantageously formed of glass, plastic, quartz, sapphire or the like.

The apparatus 10 can be used to apply an electric potential to an aqueous solution containing an analyte and an ECL label. Additionally, the apparatus 10 can be used to detect light emissions form the stimulated label. For all the experimental work disclosed herein, the apparatus 10 was used to apply a scan or sweep of voltage to the aqueous solution. Sweeping or scanning the voltage (i.e. from 0.0 v. to +1.6 v. to −1.8 v.) entails the continuous application of an electric potential to the aqueous solution during the period of current application. The voltage could alternately, and preferably, be pulsed, that is applied to the aqueous solution is short bursts of current (i.e. each voltage pulse could be initiated and concluded within about 100 micro seconds). Pulsing can permit a faster generation of ECL from a transition metal complex, and hence a faster analyte detection throughout where multiple analyte samples are to be detected and/or quantified.

The amount of light or other electromagnetic radiation emitted by the label within the aqueous solution is indicative of the presence or absence of an analyte, and, if it is present, in what amount. Thus, qualitative and quantitative analysis of a sample for an analyte of interest is enabled. In this connection, when the electromagnetic radiation emitted is light, that emission can be detected with a photomultiplier.

The electromagnetic radiation emitted when the label descends from an excited state can be detected using suitable means in order to permit a qualitative or quantitative determination of the analyte. Detection can be carried out visually in certain embodiments, but advantageously either as a continuous rate-based measurement, or as an accumulation of the ECL signal over a long period of time. For example, rate-based measurement methods can be performed with photomultiplier tubes, photodiodes or phototransistors to produce electric currents proportional in magnitude to the incident light intensity, or by using charge coupled devices, whereas examples of cumulative methods are the integration of rate-based data and the use of photographic film to provide cumulative data directly.

Within the scope of the present invention there is included a composition or kit that can be prepared to obtain the desired pH, concentration of label, concentration of ECL cofactor, concentration of ECL facilitator and of aqueous solution.

The method of the present invention can be used in a variety of analyte assay formats. Thus, the invention can be used in, for example, homogeneous or heterogeneous assay formats, forward and reverse assays, competitive binding assays, immunometric assays, sandwich assays, and hybridoma screening assays.

EXAMPLES

The following examples are set forth as illustrations of various features and embodiments of the present invention and are not intended to limit the scope of the claimed invention.

Example 1

This Example illustrates an oxidative electrochemiluminescence according to the disclosure of Leland and Powell in J. Electrochem. Soc., 1990, 173, 3127–3131 and WO 90/05296, May 17, 1990. Oxidative electrochemical luminescence of a transition metal label was detected by essentially reproducing a methodology known to the art. The ECL measurements were carried out using the apparatus shown in FIGS. 1 to 4. The same apparatus was used to obtain all the data set forth by all the Tables and all the graphs accompanying this application. This apparatus was an electrochemical optical cell set up. The cell contained the aqueous solution and had a conventional three electrode setup, working and counter gold electrodes and a reference Ag/AgCl electrode on a short arm downstream of the cell outlet. The reagents were pumped into the cell at a suitable rate by a peristaltic pump. Pumping was stopped during the measurement period.

The voltage potential applied to the aqueous solution within the cell was controlled by a potentiostat (EG&G Model 273). In this example, the Voltage was cycled from starting potential, $E_1=0$ mv to a vertex potential, $E_2=+1600$ mv, to a final potential $E_3=-900$ mv relative to a Ag/AgCl reference electrode. The voltage was scanned at 500 mv/second. Generally, measurements were made in a single first sweep. Light emission was measured by a photomultiplier tube (Hamamatsu HC124-01). Electrochemical current, and light emission were recorded on Y and Y' axes respectively as a function of applied voltage (X axis).

TPA Reagent: An aqueous solution was prepared by dissolving 20.7 g of $NaH_2PO_4 \cdot H_2O$ in 200 mL of water, followed by adding 14.326 g of tri-n-propyl amine (Aldrich) (TPA) and stirring until completely dissolved. The pH of the aqueous solution was then adjusted to 7.0 by adding dropwise a 1M solution of a phosphate buffer, $Na_2HPO_4$, To the aqueous solution there was then added 0.5 g of a wetting agent, Tween 20. The aqueous solution as then made up to a volume of 1 liter by adding water that had been reverse osmosis purified and had a resistance measurement of about 18 mega ohms.

Wash Reagent: A washing reagent was prepared as 150 mM of the phosphate buffer pH 7.5, with 0.05% Tween 20.

Luminophore Reagent: The luminophore reagent was prepared by dissolving 0.07486 mg of a tris-(2,2'-bipyridine) ruthenium (II) chloride (molecular formula: $Ru(C_{10}H_8N_2)_3Cl_2 \cdot 6H_2O$) obtained from Aesar/Johnson Mathey, Ma., in 100 mL of the TPA reagent to obtain a 1 µM solution of the ruthenium ECL label. Working solutions of the ruthenium ECL label in the concentration range of 200 pM to 800 pM were then made up by appropriate dilutions in the TPA reagent.

The gold working electrode was first pretreated by two to three repeated cyclic potential scans of +1.8 and -1.6 v to provide a reproducibly clean and reactive metal surface. Such electrochemical pretreatment is well known in the art. The electrochemical cell was then washed clean by pumping in the washing reagent. The cell was then filled with the luminophore working reagent containing a given amount of the ruthenium ECL label. Emitted light intensity was measured in triplicate for each concentration of the ruthenium ECL label used.

In this Example 1, as shown by FIG. 5, light emission from the ruthenium ECL label was detected only when the applied voltage potential was an oxidative voltage potential of greater than about +1000 mv and the light emission tracked the oxidation current and the maximum emission occurred at the oxidation potential of water. As shown by FIG. 5, no light emission was detected when the applied voltage potential was a negative or cathodic voltage potential between 0 v and -900 mv. It was determined the light emission by the ruthenium ECL label varied linearly with the ruthenium ECL label concentration in the aqueous solution. FIG. 5 also indicates that the detection limit was about 100 pM of the ruthenium ECL label due to background light emission from the reagent blank solution, i.e. in the absence of any ruthenium ECL label.

Example 2

This an example of a regenerative method of electrochemiluminescence based on cycling the gold electrode potential between oxidative and potentials sufficient to cause both oxidation and reduction. Both oxidative and reductive electrochemiluminescence of a transition metal label were detected in completely aqueous solution and without peroxydisulfate, illustrating one aspect of the present invention. The reagent solutions and experimental setup were as described in Example 1. The voltage was cycled from a starting potential of $E_1=0$ mv to a vertex potential of $E_2=+1800$ mv, to a final potential of $E_3=-1600$ mv versus a Ag/AgCl reference electrode.

FIG. 6 shows the voltammograms and simultaneous emission profiles for the ruthenium ECL label in the concentration range of 0 pM to 800 pM. Light emission was detected during the positive voltage scan portion (beginning at about +1000 mv), and surprisingly also in the negative portion of the applied voltage, beginning at about -600 mv. The reductive ECL was manifested as two distinct peaks with maximum reductive ECL emissions occurring at about -850 mv and at about -1200 mv, and the emitted light intensity varied linearly with the label concentration, as occurred with the oxidative ECL emission.

Example 3

This is an example of ECL generated by electrochemical reduction at a cathodic potential in aqueous solution in the absence of peroxydisulfate and without the removal of dissolved oxygen illustrating a second aspect of the present invention. A reductive ECL of the ruthenium ECL label was obtained in the same aqueous reagent solution used in Example 1, except that the ECL facilitator hydroxylamine hydrochloride in the concentration range of 100 µM to 20 mM was added. The general experimental setup were also as described in Example 1. The voltage applied (defined by $E_1$, $E_2$, and $E_3$) was varied according to the experiments described below:

a) At a hydroxylamine concentration of 100 µM and the aqueous solution containing 800 pM of the ruthenium ECL label, very little or no ECL was observed when the voltage scan was over the range $E_1=-500$ mv, $E_2=-1600$ mv $E_3=0$ mv versus the Ag/AgCl reference electrode.

b) At a hydroxylamine concentration of 1.0 mM, the reagent containing 800 pM of the ruthenium ECL label showed high levels of ECL when the voltage range scanned had $E_1=-500$ mv, $E_2=-1600$ mv, $E_3=0.0$ mv versus the Ag/AgCl reference electrode. Typically, the ECL peaked at a potential of about -1350 mv. FIG. 7A shows the influence of the ruthenium ECL label concentration (0 pM to 800 pM) on the ECL emission intensity. As shown in FIG. 7B, when the voltage was scanned between oxidation and reduction portions ($E_1=0.0$, $E_2=+1800$, $E_3=-1600$ mv) both the oxidative and reductive ECL emission was also observed. However, in the presence of hydroxylamine, the reductive ECL emission was significantly higher than the oxidative ECL, as well as being higher than the ECL observed with reductive ECL only. All the ECL emissions demonstrated a linear relationship with the concentration of the ruthenium ECL label used in the aqueous solution.

c) At an hydroxylamine concentration of 5.0 mM, the aqueous solution reagent containing 800 pM the ruthenium ECL label showed a significantly higher level of ECL than observed with either 1 or 10 mM of hydroxylamine. On scanning only the cathodic voltage portion ($E_1=-500$ mv, $E_2=-1600$ mv, $E_3=0.0$ mv), a well defined strong reductive ECL emission peak at an applied voltage of about −1.15 volts could be observed. However, when the voltage was scanned between +1800 to −1600 mv ($E_1=0$ mv, $E_2=+1800$ mv, $E_3=+1600$ mv) strong ECL emissions were observed at both the anodic (oxidative) and cathodic (reductive) potentials. The cathodic ECL was manifested as a double peak: a low intensity peak at about 850 mv and a high intensity peak at about 1300 mv. This was about 150 mv more negative and with a higher intensity than the one observed with a cathodic-only voltage sweep. The relationship of the ruthenium ECL label concentration (between 0 pM to 800 pM) to ECL emission intensity was determined to be linear.

d) At a hydroxylamine concentration of 10.0 mM, the reagent containing 800 pM of the ruthenium ECL label showed a very low level of ECL emission when the voltage was scanned $E_1$+−500 mv, $E_2$=−1600 mv, $E_3$=0 mv. However, when the voltage was scanned with $E_1=0$ mv, $E_2=+1600$ mv, $E_3=-1600$ mv, both the anodic (oxidative) and cathodic (reductive) ECL emissions were detected. The oxidative ECL manifested itself as a low, broad emission starting at +900 mv. However, there was significant ECL emission enhancement in the cathodic portion (−1200 mv). It was found that this reductive ECL can be further enhanced if the voltage is swept from 0.0 v. to +1800 mv to −1600 mv. Additionally, when the influence of the ruthenium ECL label concentration (0 pM to 800 pM) on these ECL emissions was investigated, it was determined that (1) when only a reductive potential was applied, there was very little cathodic ECL emission even at 800 pM concentration of the ruthenium chelate. Reductive ECL albeit at a significantly lower emission was still manifested when voltage was swept from 0.0 v. to +1800 mv to −1600 mv.

A similar study was carried out with hydroxylamine-HCl and the results are summarized in Table 4. FIG. 11 shows a linear regression plot of reductive ECL vs ruthenium ECL label concentration in 1 mM cyclohexylhydroxylamine-HCl. It is clear that hydroxylamines have an ECL moderator effect distinctly different from that of chlorides.

Example 4

In this example, ECL was generated by electrochemical reduction under an exclusively cathodic potential scan (0 v to −1.6 v). In the TPA reagent solution the sodium chloride was replaced by 1 mM of hydroxylamine-HCl. The voltage was scanned from 0.0 v. to −1.6 v. to 0.0 v. at a rate of 500 mv/second. FIG. 14 shows the voltammogram and simultaneous emission profiles for the ruthenium ECL label in the concentration range of 0 pM to 800 pM. Similar emission behavior was observed even when the voltage was scanned from −1.1 v to −1.6 v to 0.0 v. This clearly distinguishes the reductive ECL in the presence of hydroxylamine from that observed with an aliphatic amine-HCl or NaCl. A linear response of emitted ECL intensity with the ruthenium ECL label concentration with voltage scans of 0 v to −1.6 v was obtained. As shown in Table 7, emitted ECL was significantly enhanced by imposing a time delay of 5 seconds at −1.1 v.

Example 5

The reductive ECL emissions observed with hydroxylamine HCl, as set forth in Example 3, prompted a screening study to determine the possible suitability of other amines cofactors to enhance the ECL emission of the ruthenium ECL label in the TPA reagent solution prepared as set forth in Example 1. The compounds studied included those shown in Table 1. The voltage was applied and scanned in two modes. In Mode 1, the applied voltage was swept from 0.0 v. to +0.8 v. to −1.6 v. For Mode 2, the applied voltage was swept from 0.0 v. to −1.6 v to 0.0 v. The results observed are summarized in Table 1.

The following phenomena were observed. When various aliphatic amines were added to the aqueous solution, a first scan to +0.8 v (Mode 1) was required to obtain the reductive ECL. The Mode 2 scan does not produce any reductive ECL with these amines. Significantly, the +0.8 v. potential applied in Mode 1 is below the applied voltage at which oxidative ECL emission usually occurs. Optimal reductive ECL emission was determined to occur at an aliphatic amine concentration of about 10 mM.

Contrarily, when various hydroxylamines were added to the TPA reagent solution, both the Mode 1 and Mode 2 scans generated reductive ECL by the ruthenium ECL label. It is important to note that the Mode 2 scan (at which reductive ECL was observed with the hydroxylamines of Table 1 but not with the aliphatic amines set forth in Table 1) is a purely cathodic voltage scan.

With the hydroxylamines, reductive ECL emission peaks were detected at about −1.0 v. Optimal reductive ECL emission was determined to occur at a hydroxylamine concentration of about 1 mM.

All of the amines tested above had been introduced as the corresponding amine hydrochlorides, and it was suspected that the chloride ion, rather than the amine, was responsible for the enhanced ECL response observed with the amines.

The influence of adding NaCl to the TPA reagent solution was then studied. Addition of NaCl, as with the aliphatic amines, was found to produce a reductive ECL emission when a Mode 1 voltage scan was employed, but no reductive ECL emission was observed with the purely cathodic voltage scan of Mode 2.

The effect of adding from 10 mM to 200 mM of NaCl to the TPA containing aqueous solution was studied. With the Mode 1 scan, reductive ECL emission peaks were detected at about −1.25 v Optimal emission was observed at about 25 mM NaCl, as shown by FIG. 8. Unexpectedly, the addition of NaCl was found to significantly enhance the oxidative ECL: the oxidative ECL emission near +1 v was found to be almost doubled in intensity. Additionally, the applied voltage potential at which the ECL emissions occurred shifted to less positive values, as shown by Table 2. For comparison, FIG. 9 shows ECL with the same TPA reagent solution, but without any NaCl.

Upon substituting $Na_2SO_4$ for NaCl in the aqueous solution, the reductive ECL emission disappeared and there was little influence on the oxidative emission. It was therefore concluded that the reductive ECL emission effects observed, including the synergistic effects of Cl- and of the various aliphatic amines on the oxidative ECL emissions, were due to the presence of Cl- ions in the TPA reagent solution. The influence of the concentration of NaCl was then examined at a constant concentration of 800 pM of the ruthenium ECL label and three modes of voltage scan: (1) 0 v to +0.8 v to −1.6 v, (2) 0 v to +1.8 v to −0.6 v, (3) 0 v to +1.8 v to −1.6 v. Mode 1 produced only reductive ECL; Mode 2 produced only oxidative ECL, and; Mode 3 gives both oxidative and reductive ECL. ECL measurements were made in triplicate, and the results are summarized in Table 3.

FIG. 10 shows a linear regression plot of reductive ECL vs ruthenium ECL label concentration with 25 mM of NaCl being present in the aqueous solution.

Example 6

In this example, ECL emissions by the ruthenium ECL label were generated by electrochemical reduction at a cathodic potential in the TPA reagent solution containing 25 mM sodium chloride. The voltage was scanned from 0 v to +0.8 v to −1.6 v at a rate of 500 mv/second. FIG. 12 shows the voltammogram and simultaneous emission profiles for the ruthenium ECL label in the concentration range of 0 to 800 pM (triplicate measurements). The maximum reductive ECL emission was detected, as shown by FIG. 12, at about −1.3 v. Significantly, with this non-oxidative applied voltage scan (i.e. the anodic voltage applied did not exceed +0.8 v) very little light emission was observed with the reagent blank. Thus, significantly less than the minimum amount of label used, 100 pM, could be detected by this reductive ECL methodology. It is reasonable to expect, as shown by the negligible light emission from the blank, and shown in FIG. 12, that as little as about 10 pM or less of the ruthenium ECL label could be detected in the aqueous TPA reagent solution at a physiological pH with the disclosed detection methodology.

Additionally, it was discovered that, when the applied voltage potential was maintained at a steady level of +0.8 v for a period of 5 seconds during the voltage scan, such a time delay significantly enhanced the reductive ECL, as set forth by Table 5. The same effect was observed by maintaining the potential at +0.35 v. The enhanced ECL emission was determined to have a linear relationship with the ruthenium ECL label concentration in the aqueous TPA reagent solution.

Example 7

In this example, enhanced ECL emissions by the ruthenium ECL label were generated by electrochemical oxidation at an anodic potential in the TPA reagent solution containing 1 mM sodium bromide. The voltage was scanned from 0 v to +1.6 v to −0.8 v at a rate of 500 mv/second. The presence of Br⁻ ions unexpectedly increased the oxidative emission to about 10 times. The oxidative emission appears to consist to peaks—A and B centered around +0.95 v and +1.25 v respectively. Peak A at +0.95 was almost twice the height of the peak B at +1.25 v. The oxidative emission observed at +1.25 v appears to be the identical to emission reported in the prior art. We believe that the emission observed at about +0.95 v is novel and produced by bromide ion catalysis via adsorption at the surface of gold electrode. The emission intensity of the reagent blank was sufficiently low to allow a clear distinction 10 pM of the ruthenium label signal. The emission intensity (as peak heights in mv) for 0, 10, 20, 40, 80 and 100 pM of the ruthenium label was determined to be linear.

Surprisingly, this emission was completely quenched when NaBr concentration was increased to 10 mM. The effect of the addition of iodide and fluoride ions at 1 mM concentration to the TPA reagent solution were then examined. While F⁻ ions appear to have no influence on the oxidative ECL, I⁻ was found to detrimental.

A method and composition according to the present invention has many advantages, including the following:

1. The method makes use of commercially available and relatively inexpensive materials and reagents.
2. Reductive ECL can be achieved in the presence of residual oxygen in an aqueous solution.
3. Reductive ECL can be achieved in the aqueous solution without the need for any nonaqueous co-solvent, sulphur-containing compound, or any peroxy compound in the aqueous solution.
4. Reductive ECL can be achieved in an aqueous solution at a physiological pH.
5. An analyte can be detected at a concentration of about 10 picomoles per liter (or less) of aqueous solution.
6. The reductive ECL can be generated and measured by sweeping the electrochemical potential in the cathodic portion only in the presence of a hydroxylamine as an ECL cofactor, or by sweeping the electrochemical potential in the anodic and cathodic potentials sequentially, or by pulsing the electrode repetitively between anodic and cathodic potentials in the presence of a halide as an ECL facilitator.
7. The method does not require use of any radioisotopes.
8. The ECL labels used are stable and have long shelf lives at room temperature.
9. The ECL labels used are versatile and can be used to detect a variety of analytes.
10. The method can be used in a wide variety of analyte detection techniques, including immunoassay and nucleic acid probe assays.
11. Analyte detection is rapid, as only a few seconds are required for analyte detection.
12. No organic cosolvent is required in the aqueous reagent solution containing the transition metal ECL label to generate a reductive ECL emission.

Although the present invention has been described in considerable detail with regard to certain preferred embodiments thereof, other embodiments within the scope of the teachings of the present invention are possible. For example, the disclosed method and composition can be used with a diversity of ECL labels.

Accordingly, the spirit and scope of the appended claims should not be limited to the descriptions of the preferred embodiments contained herein.

TABLE 1

Screening Study of Aliphatic Amine Compounds for the Production of Reductive ECL.

| Compound | Voltage Scan: Volts vs Ag/AgCl | |
|---|---|---|
| | 0, +0.8, −1.6 ECL Emission Reductive | 0, −1.6, 0 ECL Emission Reductive |
| Methylamine-HCl | Yes | No |
| Trimethylamine-HCl | Yes | No |
| Ethylamine-HCl | Yes | No |
| Triethylamine-HCl | Yes | No |
| Propylamine-HCl | Yes | No |
| Hydroxylamine-HCl | Yes | Yes |
| N-Cyclohexyl-Hydroxylamine-HCl | Yes | Yes |
| N-tertbutyl-Hydroxylamine-HCl | Yes | Yes |
| N-methyl-Hydroxylamine-HCl | Yes | Yes |
| N-Isopropyl-Hydroxylamine-HCl | Yes | Yes |
| NaCl | Yes | No |

Note: R-amines 10 mM; R-Hydroxylamines 1 mM, added to the TPA reagent containing 100 mM tripropylamine in 150 mM phosphate buffer pH 7.0 and 0.05% Tween-20

TABLE 2

Influence of NaCl concentration (mM) on potential of ECL emission at 800 pM of the ruthenium ECL label
Voltage Scans:
Reductive: 0.0 to +0.80 to −1.6 volts vs. Ag/AgCl
Oxidative: 0.0 to +1.80 to −0.6 volts vs Ag/AgCl.

| NaCl (mM) | 00 | 10 | 25 | 50 | 100 | 200 |
|---|---|---|---|---|---|---|
| Oxidative ECL | +0.95 | +0.90 | +0.87 | +0.85 | +0.83 | +0.80 |
| Reductive ECL | N/A | −1.25 | −1.25 | −1.25 | −1.20 | −1.20 |

TABLE 3

Influence of Sodium Chloride Concentration on Reductive and Oxidative ECL at 800 pM of Ruthenium tris-bipyridyl-HCl (peak area × 1000)

| | Voltage Scan: Volts vs Ag/AgCl | | | |
|---|---|---|---|---|
| | 0, +0.8, −1.6 ECL emission | 0, +1.8, −0.6 ECL emission | 0, +1.8, −1.6 ECL emission | |
| NaCl (mM) | Reduction | Oxidation | Oxidation | Reduction |
| 0 | 0 | 52.17 | 69.15 | 58.8 |
| | | 52.63 | 66.38 | 64.18 |
| | | 59.07 | 67.33 | 62.42 |
| 10 Mm | 42.14 | 93.8 | 113.89 | 72.37 |
| | 42.48 | 93.16 | 119.04 | 71.27 |
| | 43.56 | 94.3 | 120.75 | 69.73 |
| 25 mM | 44.3 | 105.76 | 136.86 | 61.09 |
| | 46.37 | 114.97 | 139.74 | 59.91 |
| | 44.9 | 116.39 | 139.57 | 62.92 |
| 50 mM | 44.43 | 120.52 | 133.55 | 48.64 |
| | 42.58 | 121.42 | 132.33 | 52.51 |
| | 42.23 | 121.37 | 131.86 | 48.53 |
| 100 Mm | 34.03 | 49.6 | 60.38 | 33.67 |
| | 34.34 | 52.32 | 59.83 | 31.08 |
| | 34.2 | 52.49 | 60.83 | 33.33 |
| 200 mM | 26.88 | 27.85 | 35.7 | 21.22 |
| | 25.88 | 28.63 | 33.63 | 23.02 |
| | 25.55 | 29.43 | 35.59 | 20.75 |

TABLE 4

Influence of Hydroxylamine-HCl concentration on Reductive and Oxidative ECL at 800 pM of ruthenium tris-bipyridyl Emission = Peak area × 1000

| | Voltage Scan: Volts vs Ag/AgCl | | |
|---|---|---|---|
| | 0, −1.6, 0 | 0, +1.8, −1.6 | |
| Hydroxylamine HCl (mM) | ECL emission Reduction | ECL Oxidation | Emission Reduction |
| 0 | 0 | 69.15 | 58.8 |
| | 0 | 66.38 | 64.18 |
| | 0 | 67.33 | 62.42 |
| 1 | 53.95 | 77.94 | 72.97 |
| | 49.77 | 84.37 | 75.02 |
| | 50.91 | 83.25 | 74.27 |
| 5 | 13.34 | 24.19 | 41.66 |
| | 13.71 | 25.26 | 43.18 |
| | 14.19 | 25.34 | 43.37 |
| 10 | 2.45 | 0 | 17.65 |
| | 2.44 | 0 | 18.62 |
| | 3.29 | 0 | 19.44 |

TABLE 5

Comparison of Reductive ECL Emission with and without 5 second delay at +0.8 v during voltage scan (0.0 to +0.8 to −1.6 v). Reagent: 150 mM phosphate buffer pH 7.0 containing 100 mM TPA, 0.05% Tween 20, and 25 mM sodium chloride. Emissions measured as peak heights in mv.
N = 3 (± Std. Dev.)

| Ru ECL label (pM) | ECL Emission zero delay | ECL Emission 5 s delay +0.8 v |
|---|---|---|
| Reagent Blank | ≅0 | ≅0 |
| 100 | 0.307 (± 0.066) | 0.503 (± 0.009) |
| 200 | 0.910 (± 0.05) | 0.967 (± 0.024) |
| 400 | 1.843 (± 0.066) | 1.967 (± 0.034) |
| 600 | 2.690 (± 0.057) | 2.907 (± 0.039) |
| 800 | 3.577 (0.056) | 3.740 (± 0.029) |

TABLE 6

Comparison of Reductive ECL Emission with and without 5 second delay at +0.4 v during voltage scan (0.0 to +0.4 to −1.6 v). Reagent: 150 mM phosphate buffer pH 7.0 containing 100 mM TPA, 0.05% Tween 20, and 10 mM Ethylamine-HCl. Emissions measured as peak heights in mv.
N = 3 (± Std. Dev.)

| Ru ECL label (pM) | ECL Emission zero delay | ECL Emission 5 s delay +0.4 v |
|---|---|---|
| Reagent Blank | ≅0 | ≅0 |
| 100 | ≅0 | 0.677 (± 0.062) |
| 200 | 0.723 (± 0.162) | 1.310 (± 0.037) |
| 400 | 1.850 (± 0.085) | 2.593 (± 0.038) |
| 600 | 2.463 (± 0.111) | 3.427 (± 0.237) |
| 800 | 3.613 (0.029) | 4.953 (± 0.180) |

TABLE 7

Comparison of Reductive ECL Emission with and without 5 second delay at −1.1 v during voltage scan (−1.1 to −1.6 to 0.0 v). Reagent: 150 mM phosphate buffer pH 7.0 containing 100 mM TPA, 0.05% Tween 10, and 1 mM hydroxylamine-HCl. Emissions measured as peak heights in millivolts (mv) N = 3 (± Std. Dev.)

| Ru ECL label (pM) | ECL Emission zero delay | ECL Emission 5 s delay −1.1 v |
|---|---|---|
| Reagent Blank | 0.225 (± 0.005) | 0.225 (± 0.005) |
| 100 | 0.620 (± 0.028) | 0.617 (± 0.005) |
| 200 | 1.357 (± 0.037) | 1.733 (± 0.063) |
| 400 | 2.303 (± 0.153) | 2.753 (± 0.083) |
| 600 | 3.357 (± 0.205) | 4.030 (± 0.144) |
| 800 | 4.353 (0.197) | 5.037 (± 0.162) |

We claim:

1. A method for detecting an analyte, comprising the steps of:

a) adding a label, an hydroxylamine, and an analyte of an aqueous solution;

b) stimulating the label to emit electromagnetic radiation in an electrochemical luminescence reaction, in the absence of applying an oxidative potential by applying a reducing potential to the aqueous solution, and;

(c) detecting the analyte by detecting the electromagnetic radiation emitted by the label.

2. The method of claim 1, further comprising the step of quantifying the amount of the analyte.

3. The method of claim 1, wherein the analyte is added to the aqueous solution in a sample of a physiological fluid.

4. The method of claim 1, wherein the aqueous solution has a physiological pH.

5. The method of claim 1, wherein the aqueous solution has a pH between about 6 and about 8.

6. The method of claim 1, wherein the aqueous solution has a physiological pH that is maintained by addition of a suitable buffer to the aqueous solution prior to the adding step.

7. The method of claim 1, wherein the aqueous solution is at least about 95% by weight water.

8. The method of claim 1, wherein the aqueous solution is at least about 98% by volume water.

9. The method of claim 1, wherein the label comprises a transition metal.

10. The method of claim 1, wherein the label comprises an organic ligand.

11. The method of claim 9 wherein the transition metal is selected from the group consisting of chromium, ruthenium, rhodium, rhenium, osmium and iridium.

12. The method of claim 1, wherein the electromagnetic radiation is emitted as light in the visible spectrum.

13. The method of claim 1, wherein the electromagnetic radiation emitted has an emission maximum at a wavelength between about 200 nm and about 900 nm.

14. The method of claim 1, Wherein the reducing potential applied to the aqueous solution is at least about −600 millivolts.

15. The method of claim 1, wherein the method further comprises the step of adding an amine to the aqueous solution prior to the stimulating step.

16. The method of claim 15, wherein the amine is a tri-n-propylamine.

17. The method of claim 1, wherein the hydroxylamine is selected from the group consisting of hydroxylamine, N-cyclohexyl-hydroxylamine, N-tertbutyl-hydroxylamine, N-methylhydroxylamine, and N-isopropyl-hydroxylamine.

18. The method of claim 1 further including a halide ion.

19. The method of claim 1, further comprising the step of applying a positive potential to the aqueous solution prior to application of the reducing potential to the aqueous solution.

20. The method of claim 19 wherein the positive potential applied to the aqueous solution is an oxidative potential.

21. The method of claim 20, wherein the oxidative potential applied to the aqueous solution is at least about +800 millivolts.

22. A method for detecting an analyte, comprising the steps of:
(a) preparing an aqueous solution comprising a suitable buffer for maintaining the aqueous solution at a physiological pH:
(b) selecting a label comprising a transition metal and an organic ligand chelated to the transition metal, the label being capable of emitting electromagnetic radiation with an emission maximum between about 200 nm and about 900 nm in an electrochemical luminescence reaction;
(c) adding:
  (i) an analyte present in a sample of a physiological fluid,
  (ii) the label,
  (iii) an amine and,
  (iv) an ECL facilitator selected from the group consisting of halides and hydroxylamines, to the aqueous solution, the aqueous solution thereby comprising at least about 95% by weight water and at least about 98% by volume water;
(d) stimulating the label to emit electromagnetic radiation in an electrochemical luminescence reaction, in the absence of applying an oxidative potential by applying a reducing potential to the aqueous solution,
(e) detecting the presence or the absence of the analyte by detecting the electromagnetic radiation; and
(f) quantifying the amount of analyte present in the sample of the physiological fluid.

23. The method of claim 22, wherein the amine comprises a tri-n-propylamine.

24. The method of claim 22, wherein the ECL facilitator comprises a halide.

25. The method of claim 22, wherein the electric potential applied to the aqueous solution is an oxidative potential.

26. The method of claim 22, wherein the oxidative potential applied to the aqueous solution is less than about +1 volt.

27. The method of claim 22, wherein the oxidative potential applied to the aqueous solution is less than about +0.9 volts.

28. The method of claim 22, wherein the oxidative potential applied to the aqueous solution is between about +1.3 volts and about +0.7 volts.

29. The method of claim 22, wherein the oxidative potential applied to the aqueous solution is between about +1.3 volts and about +0.9 volts.

30. The method of claim 22, wherein the oxidative potential applied to the aqueous solution is between about +1 volt and about +0.9 volts.

31. The method of claim 22, wherein the electric potential is a reducing potential.

32. The method of claim 22, wherein a reducing potential is applied to the aqueous solution subsequent to application of the oxidative potential.

33. The method of claim 22, wherein less than about 10 pM of the analyte can be detected.

34. The method of claim 22, wherein the stimulating step comprises the step of maintaining the electric potential at a substantially constant voltage for at time period of between about two and about thirty seconds to enhance the emission of the electromagnetic radiation by the label.

35. The method of claim 34 wherein the electric potential is maintained for about five seconds.

36. A method for detecting a transition metal complex, comprising the steps of:
(a) adding a transition metal complex and an hydroxylamine to an aqueous solution;
(b) stimulating the transition metal complex to emit electromagnetic radiation in an electrochemical luminescence reaction, in the absence of applying an oxidation potential by applying a reducing potential to the aqueous solution, and;
(c) detecting the transition metal complex by detecting the electromagnetic radiation emitted by the transition metal complex.

* * * * *